(12) United States Patent
Sato

(10) Patent No.: US 9,931,096 B2
(45) Date of Patent: *Apr. 3, 2018

(54) RADIOGRAPHIC SYSTEM, DRIVE CONTROL METHOD FOR RADIOGRAPHIC SYSTEM, RECORDING MEDIUM FOR DRIVE CONTROL PROGRAM AND RADIOLOGICAL IMAGE DETECTION DEVICE

(71) Applicant: FUJIFILM Corporation, Tokyo (JP)

(72) Inventor: Masaru Sato, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 200 days.

This patent is subject to a terminal disclaimer.

(21) Appl. No.: 14/989,479

(22) Filed: Jan. 6, 2016

(65) Prior Publication Data

US 2016/0113616 A1    Apr. 28, 2016

Related U.S. Application Data

(63) Continuation of application No. 13/773,673, filed on Feb. 22, 2013, now Pat. No. 9,259,201.

(30) Foreign Application Priority Data

Feb. 24, 2012   (JP) ................................. 2012-038215

(51) Int. Cl.
    *A61B 6/00*    (2006.01)
(52) U.S. Cl.
    CPC ............ *A61B 6/542* (2013.01); *A61B 6/4233* (2013.01)
(58) Field of Classification Search
    CPC .................................. A61B 6/542; H05G 1/42
    See application file for complete search history.

(56) References Cited

U.S. PATENT DOCUMENTS

| 4,845,771 A | 7/1989 | Wislocki et al. |
| 5,877,501 A | 3/1999 | Ivan et al. |

(Continued)

FOREIGN PATENT DOCUMENTS

| CN | 102315233 A | 1/2012 |
| JP | 2-21597 A | 1/1990 |

(Continued)

OTHER PUBLICATIONS

Chinese Notice of Reasons for Rejection for Chinese Application No. 201310054752.1, dated Nov. 2, 2015, along with an English translation thereof.

*Primary Examiner* — Glen Kao
(74) *Attorney, Agent, or Firm* — Birch, Stewart, Kolasch & Birch, LLP

(57) ABSTRACT

It is possible to reliably avoid a problem that radiation irradiation does not stop even when an accumulated radiation dose reaches a target radiation dose. An AEC unit starts monitoring an integrated value of a radiation dose detection signal from a detection pixel and an output of an irradiation continuation signal at the same time, and continuously transmits the irradiation continuation signal in a predetermined period while the integrated value does not reach a threshold value. When the integrated value reaches the threshold value, the output of the irradiation continuation signal is stopped. The irradiation continuation signal is transmitted to an irradiation signal I/F of a radiation source control device through an irradiation signal I/F by wireless. The radiation source control device stops X-ray irradiation by an X-ray source when the irradiation signal I/F does not receive the irradiation continuation signal.

22 Claims, 15 Drawing Sheets

(56) References Cited

U.S. PATENT DOCUMENTS

| | | |
|---|---|---|
| 9,259,201 B2 * | 2/2016 | Sato ................... A61B 6/542 |
| 2007/0291904 A1 | 12/2007 | Takenaka et al. |
| 2008/0307449 A1 | 12/2008 | Stobbe et al. |
| 2009/0201841 A1 | 8/2009 | Tachikawa |
| 2010/0123083 A1 | 5/2010 | Petrick et al. |
| 2011/0164723 A1 | 7/2011 | Park et al. |
| 2012/0001080 A1 | 1/2012 | Okada |
| 2012/0250826 A1 | 10/2012 | Watanabe et al. |

FOREIGN PATENT DOCUMENTS

| | | |
|---|---|---|
| JP | 2006-68507 A | 6/2006 |
| JP | 2006-141729 A | 6/2006 |
| JP | 2008-237684 A | 10/2008 |
| JP | 2010-75556 A | 4/2010 |
| JP | 2011-153876 A | 8/2011 |
| WO | WO 2011/064968 A1 | 6/2011 |

* cited by examiner

FIG. 6

| RADIOGRAPHING REGION | TUBE VOLTAGE (kV) | TUBE CURRENT (mA) | LIGHTING FIELD | IRRADIATION STOP THRESHOLD VALUE |
|---|---|---|---|---|
| ... | ... | ... | ... | ... |
| CHEST REGION AP | V1 | I1 | ▣ | th1 |
| CHEST REGION PA | V2 | I2 | ▣ | th2 |
| ... | ... | ... | ... | ... |

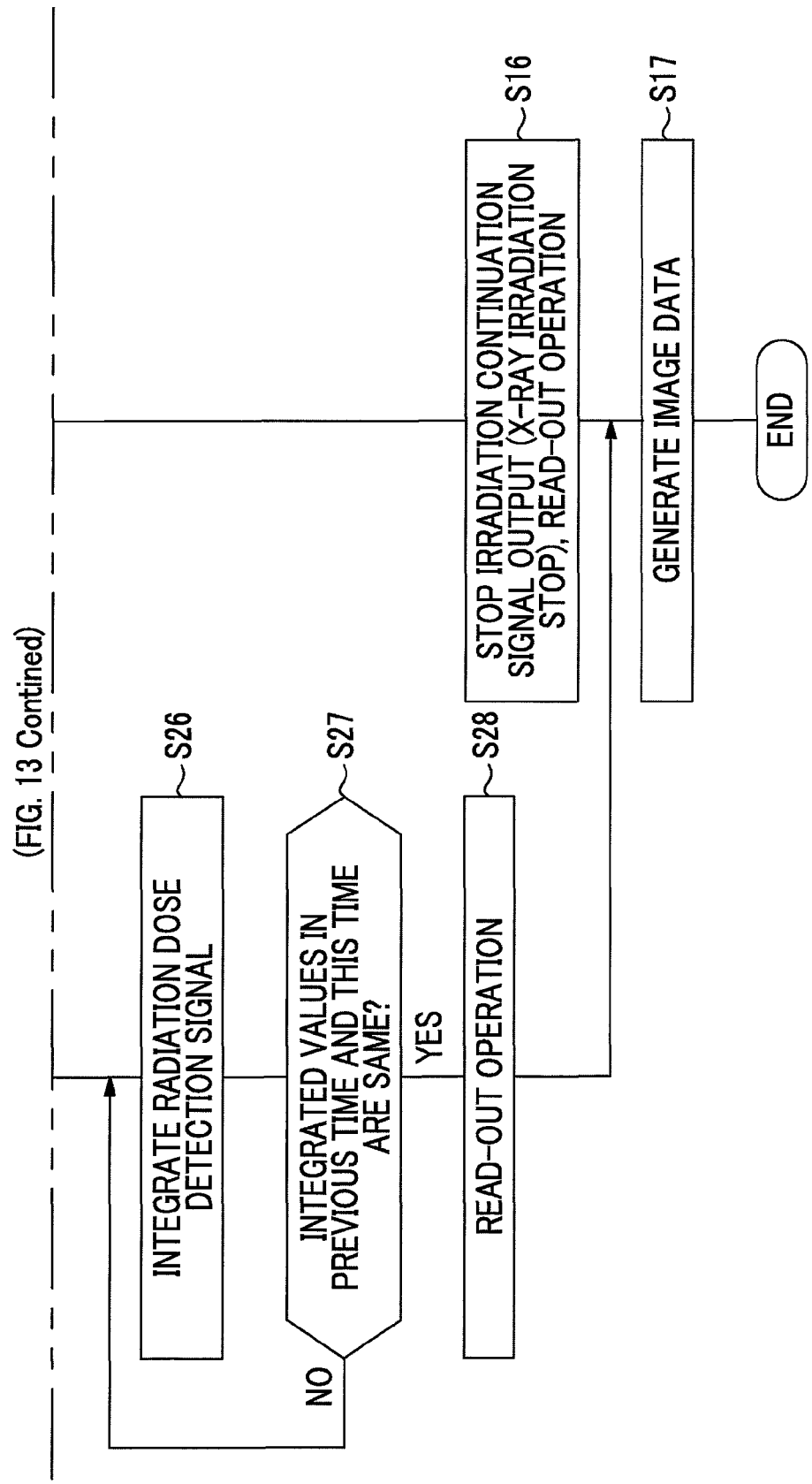

RADIOGRAPHIC SYSTEM, DRIVE CONTROL METHOD FOR RADIOGRAPHIC SYSTEM, RECORDING MEDIUM FOR DRIVE CONTROL PROGRAM AND RADIOLOGICAL IMAGE DETECTION DEVICE

CROSS-REFERENCE TO RELATED APPLICATIONS

This application is a Continuation of copending application Ser. No. 13/773,673, filed on Feb. 22, 2013, which claims priority under 35 U.S.C. § 119(a) to Application No. 2012-038215, filed in Japan on Feb. 24, 2012, all of which are hereby expressly incorporated by reference into the present application.

BACKGROUND OF THE INVENTION

1. Field of the Invention

The present invention relates to a radiographic system which performs automatic exposure control, a drive control method for a radiographic system, a drive control program and a radiological image detection device.

2. Description of the Related Art

In the medical field, an X-ray radiographic system that uses radiation such as X-rays is known. The X-ray radiographic system includes an X-ray generation device which generates X-rays and an X-ray radiographic device which receives X-rays and radiographs an X-ray image. The X-ray generation device has an X-ray source which irradiates a subject with X-rays, a radiation source control device which controls the driving of the X-ray source and an irradiation switch for inputting an X-ray irradiation start instruction. The X-ray radiographic device has an X-ray image detection device which receives X-rays that have passed through the subject and detects an X-ray image and a console which controls the driving of the X-ray image detection device.

In the X-ray radiographic system field, recently, an X-ray image detection device using a flat panel detector (FPD) as a detection panel has been commonly used instead of an X-ray film or an imaging plate (IP). The FPD has pixels which accumulate signal charge according to a reached X-ray dose and are arranged in a matrix shape. The FPD accumulates the signal charge in every pixel and the accumulated signal charge is converted to a voltage signal by a signal processing circuit so as to detect an X-ray image showing the image information of the subject and output the image as digital image data.

An electronic cassette (portable X-ray image detection device) in which the FPD is built in a rectangular parallelepiped-shaped case has also been put to practical use. Unlike a fixed type cassette which is fixed to a radiographic stand and cannot be removed from the radiographic stand, the electronic cassette is used by being detachably attached on an existing radiographic stand for a film cassette or an IP cassette and on an exclusive radiographic stand, and is used by being disposed above a bed or making the subject themself hold the cassette to radiograph a region in which radiography is difficult in the fixed type cassette. In addition, the electronic cassette is taken out of a hospital and used in a place where radiographic stand facilities are not present in some cases to radiograph the elderly convalescing at home, and an emergency patient due to an accident, a disaster or the like.

Moreover, a radiation dose detection sensor which detects the radiation dose of the X-rays that have passed through a subject is provided, and when an integrated value (accumulated radiation dose) of the radiation dose detected by the radiation dose detection sensor reaches a threshold value set beforehand, X-ray irradiation from the X-ray source is stopped and automatic exposure control (AEC) which makes the transition from an accumulation operation to a reading operation is performed in the X-ray image detection device.

An X-ray apparatus which includes a radiation dose detection sensor (light receiving unit) that detects a passed X-ray dose and an AEC unit (phototimer circuit) that determines an X-ray irradiation stop by comparing a detection result of the radiation dose detection sensor and a threshold value (reference value) is disclosed in JP1990-021597A (JP-H02-021597A). When the detection result of the radiation dose detection sensor reaches the threshold value, an X-ray cutoff request signal is output. The radiation source control device receives the X-ray cutoff request signal to stop the X-ray irradiation. In addition, a radiation dose detection sensor which transmits an irradiation stop signal to a radiation source control device (X-ray irradiation device) wirelessly and an AEC unit (phototimer) are disclosed in JP2006-068507A.

SUMMARY OF THE INVENTION

In AEC, when the X-ray irradiation is not stopped irrespective of reaching a target radiation dose, a patient is exposed to unnecessary radiation so that there has been a demand to reliably and swiftly stop X-ray irradiation when the irradiation reaches the target radiation dose. However, when the radiation source control device receives the "irradiation stop signal", the X-ray irradiation is stopped in the related art. Accordingly, in a case where the reception of the "irradiation stop signal" is difficult due to communication failure, a problem that arises is that the X-ray irradiation is not stopped irrespective of reaching the target radiation dose.

In JP1990-021597A (JP-H02-021597A), when the detection amount of the radiation dose detection sensor is equal to or more than a predetermined value, the X-ray cutoff request signal is transmitted to the radiation source control device and the X-ray irradiation is stopped. For this reason, it is necessary for the radiation source control device to receive the X-ray cutoff request signal in order to stop the X-ray irradiation. In JP2006-068507A, when the radiation source control device does not receive the irradiation stop signal, the X-ray irradiation is not stopped in the same manner. Due to this, even when the radiation source control device does not receive the signal relating to the irradiation stop due to communication failure and the like and an accumulated radiation dose reaches the target radiation dose in both cases, a problem that the X-ray irradiation is not stopped may occur. Since the signal is exchanged by wireless communication in which communication failure is easy to occur in JP2006-068507A, a possibility of a problem arising in that the X-ray irradiation is not stopped irrespective of reaching the target radiation dose is relatively high.

In order to solve the above problem, an object of the present invention is to provide a radiographic system which can reliably avoid a problem that X-ray irradiation is not stopped even when an accumulated radiation dose reaches a target radiation dose and in which a patient is not exposed to unnecessary radiation, a drive control method for a radiographic system, a drive control program and a radiological image detection device.

According to an embodiment of the invention, there is provided a radiographic system including a radiation source which irradiates a subject with radiation; a control device which controls a start and stop of radiation irradiation by the radiation source; a radiological image detection device having a detection panel in which pixels accumulating charge according to a reached radiation dose are arranged; a radiation dose detection sensor which detects the reached radiation dose; and an automatic exposure control unit which compares an integrated value of the reached radiation dose detected by the radiation dose detection sensor and a threshold value set beforehand, and determines whether the integrated value of the reached radiation dose reaches a target value based on the comparison result, wherein the automatic exposure control unit continuously transmits an irradiation continuation signal which makes the radiation source continue radiation irradiation to the control device in a predetermined period until it is determined that the integrated value of the reached radiation dose reaches the target value from the start of the radiation irradiation by the radiation source, and the control device stops the radiation irradiation when the irradiation continuation signal is not received.

The automatic exposure control unit transmits and receives the irradiation continuation signal to and from the control device wirelessly. For example, the automatic exposure control unit and the control device exchange the irradiation continuation signal by ad-hoc communication. Alternatively, the automatic exposure control unit and the control device exchange the irradiation continuation signal by a beacon.

The control device is a radiation source control device which is connected with the radiation source and controls driving of the radiation source. Alternatively, the control device is a detection control device which is connected with the radiological image detection device and controls driving of the radiological image detection device, and transmits a signal synchronized with the irradiation continuation signal to a radiation source control device which is connected with the radiation source and controls driving of the radiation source. In the latter case, the detection control device transmits and receives the signal synchronized with the irradiation continuation signal to and from the radiation source control device by wire. In addition, an irradiation stop signal which stops radiation irradiation may be transmitted from the detection control device to a radiation source control device which is connected with the radiation source and controls driving of the radiation source by wire when the detection control device does not receive the irradiation continuation signal.

The automatic exposure control unit provides an ID of the radiological image detection device in use to the irradiation continuation signal, and the control device includes a storage unit that stores an ID of the radiological image detection device in use, which is acquired separately from the irradiation continuation signal, and a collation unit that collates the ID stored in the storage unit with the ID provided to the received irradiation continuation signal and determines whether the received irradiation continuation signal is transmitted to the collation unit itself.

It is preferable to provide an irradiation stop determination unit which determines that the radiation irradiation from the radiation source is stopped based on the reached radiation dose detected by the radiation dose detection sensor. In this case, it is preferable to provide a warning display unit which notifies, when the irradiation stop determination unit determines that the radiation irradiation is stopped before the integrated value of the reached radiation dose reaches a target value, the purport to an operator. In addition, when the irradiation stop determination unit determines that the radiation irradiation is stopped before the integrated value of the reached radiation dose reaches a target value, the control device controls driving of the radiation source so that a subject is additionally irradiated with radiation that makes up for a shortage of the reached radiation dose.

The radiation dose detection sensor and the automatic exposure control unit are built in the radiological image detection device. The radiation dose detection sensor is a part of the pixels.

The radiological image detection device performs a communication function of a signal between the automatic exposure control unit and the control device and a communication function of other signals with one communication I/F. In this case, the communication I/F is capable of changing a communication speed such that the signal communication between the automatic exposure control unit and the control device is performed at a high speed and other signal communication is performed at a low speed in comparison with the case of the signal between the automatic exposure control unit and the control device.

Alternatively, the radiological image detection device performs a communication function of a signal between the automatic exposure control unit and the control device and a communication function of other signals with separate communication I/Fs. In this case, when the communication of the signal between the automatic exposure control unit and the control device is performed, the communication I/F function of other signals is stopped.

The radiological image detection device is an electronic cassette in which the detection panel is contained in a portable case.

According to another embodiment, there is provided a drive control method for a radiographic system having a radiation source which irradiates a subject with radiation, a control device which controls a start and stop of radiation irradiation by the radiation source, a radiological image detection device having a detection panel in which pixels accumulating charge according to a reached radiation dose are arranged, a radiation dose detection sensor which detects the reached radiation dose, and an automatic exposure control unit which compares an integrated value of the reached radiation dose detected by the radiation dose detection sensor and a threshold value set beforehand, and determines whether the integrated value of the reached radiation dose reaches a target value based on the comparison result, the method including continuously transmitting an irradiation continuation signal which makes the radiation source continue radiation irradiation to the control device from the automatic exposure control unit in a predetermined period until it is determined that the integrated value of the reached radiation dose reaches the target value from the start of the radiation irradiation by the radiation source; and making the control device stop the radiation irradiation when the control device does not receive the irradiation continuation signal.

According to still another embodiment, there is provided a non-transitory computer readable recording medium which records a drive control program of a radiographic system including a radiation source which irradiates a subject with radiation, a control device which controls a start and stop of radiation irradiation by the radiation source, a radiological image detection device having a detection panel in which pixels accumulating charge according to a reached radiation dose are arranged, a radiation dose detection sensor which detects the reached radiation dose, and an automatic exposure control unit which compares an integrated value of the reached radiation dose detected by the radiation dose detection sensor and a threshold value set beforehand, and determines whether the integrated value of the reached radiation dose reaches a target value based on the comparison result, the program causing a computer to execute functions of continuously transmitting an irradiation continuation signal which makes the radiation source continue radiation irradiation to the control device from the automatic exposure control unit in a predetermined period until it is determined that the integrated value of the reached radiation dose reaches the target value from the start of the radiation irradiation by the radiation source; and making the control device stop the radiation irradiation when the control device does not receive the irradiation continuation signal.

According to still another embodiment, there is provided a radiological image detection device having a detection panel in which pixels accumulating charge according to a reached radiation dose are arranged, the device including an automatic exposure control unit which compares an integrated value of the reached radiation dose detected by a radiation dose detection sensor and a threshold value set beforehand, and determines whether the integrated value of the reached radiation dose reaches a target value based on the comparison result, wherein the automatic exposure control unit continuously transmits an irradiation continuation signal which makes the radiation source continue radiation irradiation to a control device that controls a start and stop of radiation irradiation by a radiation source in a predetermined period until it is determined that the integrated value of the reached radiation dose reaches the target value from the start of the radiation irradiation by the radiation source.

In the present invention, the automatic exposure control unit continuously transmits the irradiation continuation signal to the control device until it is determined that the integrated value of the reached radiation dose reaches the target value from the start of the radiation irradiation, and it is determined that the irradiation is stopped when the irradiation continuation signal is not received in the control device so that the radiation irradiation is stopped. Therefore, even when the irradiation stop signal is not transmitted to the control device due to communication state deterioration and the accumulated radiation dose reaches the target radiation dose or more, it is possible to reliably avoid a problem that the radiation irradiation does not stop and there is no concern that a patient is exposed to unnecessary radiation.

BRIEF DESCRIPTION OF THE DRAWINGS

FIG. 6 is a view showing radiographing conditions set by a console.

DESCRIPTION OF THE PREFERRED EMBODIMENTS

Figure 1:
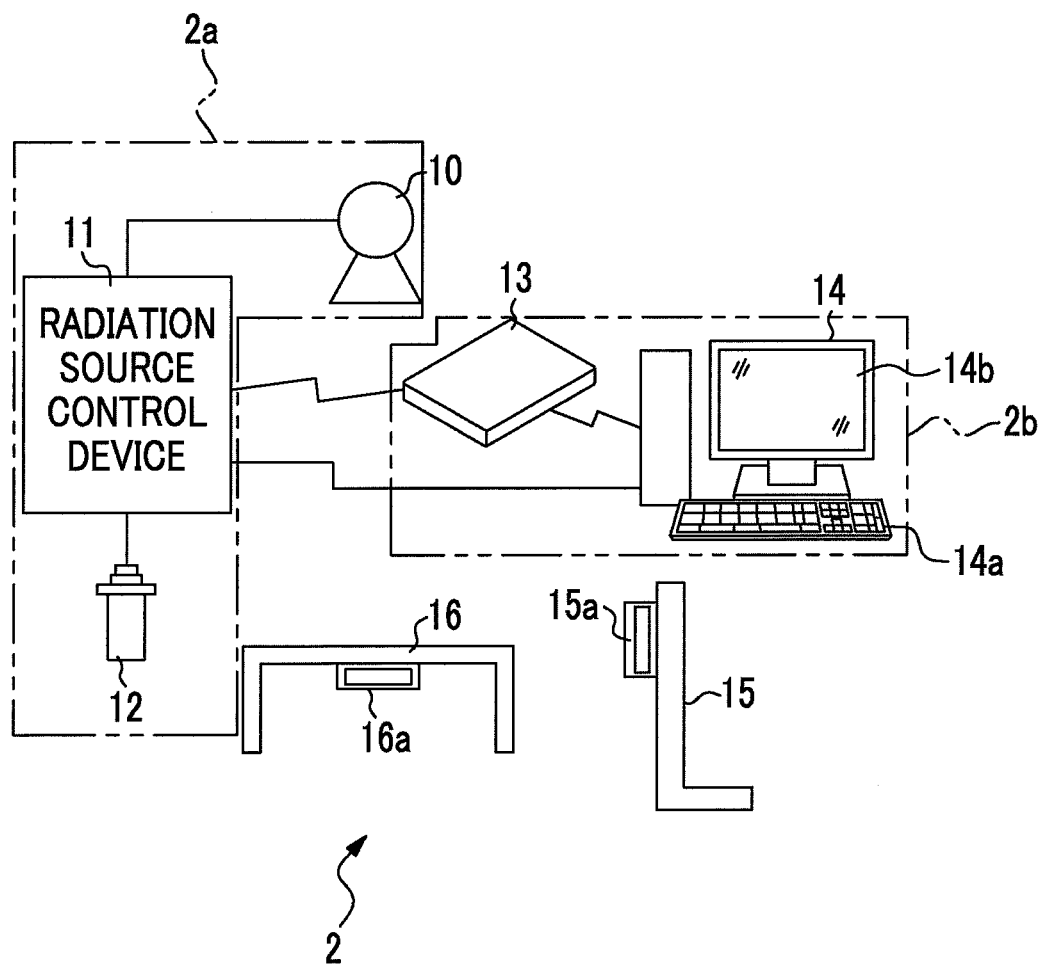
FIG. 1 is a schematic view showing a configuration of an X-ray radiographic system.

In FIG. 1, an X-ray radiographic system 2 has an X-ray source 10 in which an X-ray tube radiating X-rays is built, a radiation source control device 11 which controls the operations of the X-ray source 10, an irradiation switch 12 for instructing a start of the X-ray irradiation, an electronic cassette 13 which detects the X-ray passed through a subject and outputs an X-ray image, a console 14 (corresponding to a detection control device) which performs the operation control of the electronic cassette 13 and an image process of an X-ray image, an upright radiographic stand 15 for radiographing a subject in an upright posture, and a supine radiographic stand 16 for radiographing a subject in a supine posture. The X-ray source 10, the radiation source control device 11 and the irradiation switch 12 configure an X-ray generation device 2a, and the electronic cassette 13 and the console 14 configure an X-ray radiography device 2b, respectively. In addition, a radiation source moving device (not shown) for setting the X-ray source 10 in a desired direction and a desired position is provided.

The X-ray source 10 has the X-ray tube which radiates X-rays and an irradiation field limiter (collimator) which limits an irradiation field of X-rays radiated from the X-ray tube. The X-ray tube has a cathode made of filament which emits thermal electrons and an anode (target) which radiates X-rays after collision of the thermal electrons emitted from the cathode. The irradiation field limiter is made of, for example, plural lead plates for shielding X-rays arranged in parallel crosses and an irradiation opening for transmitting X-rays is formed in the middle of the irradiation field limiter, in which the size of the irradiation opening is changed by moving the position of the lead plates to limit the irradiation field.

Figure 2:
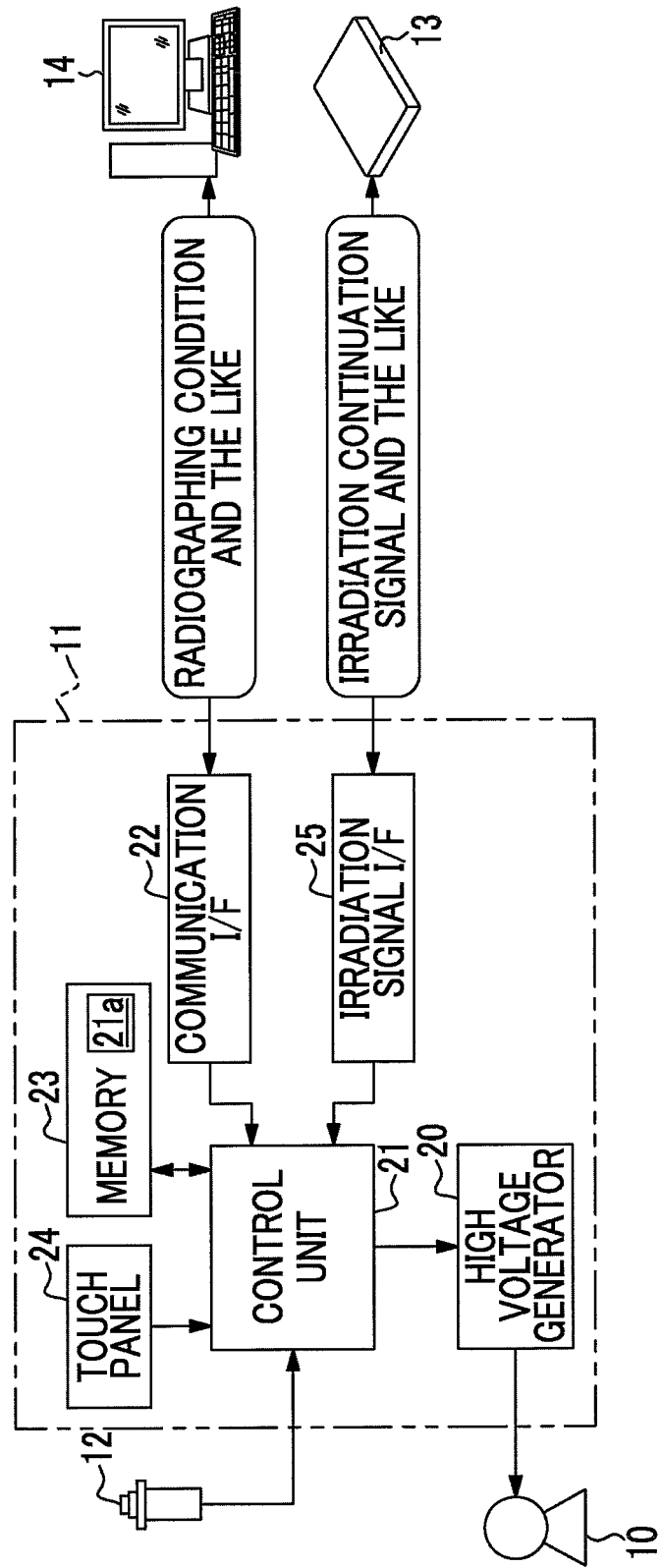
FIG. 2 is view showing an internal configuration of a radiation source control device and a connection relationship of the radiation source control device and other devices.

As shown in FIG. 2, the radiation source control device 11 includes a high voltage generator 20 which boosts input voltage by a transformer, generates high-tube voltage, and supplies the voltage to the X-ray source 10 through a high voltage cable, a control unit 21 which controls tube voltage determining an energy spectrum of the X-ray radiated by the X-ray source 10, a tube current determining an irradiation amount per unit time, and the irradiation time of X-rays based on a drive control program 21a stored in a memory 23, and a communication I/F 22 which mediates transmitting and receiving of important information and signals with the console 14.

The control unit 21 is connected with the irradiation switch 12, the memory 23 and a touch panel 24. For example, the irradiation switch 12 is a two-stage push switch which is operated by an operator such as a radiographer. When being pressed one stage, the irradiation switch generates a warm-up start signal for starting warm-up of the X-ray source 10, and when being pressed two stages, the irradiation switch generates an irradiation start signal for starting irradiation from the X-ray source 10. These signals are input to the radiation source control device 11 through the signal cable. When the irradiation start signal is received from the irradiation switch 12, the control unit 21 starts power supply to the X-ray source 10 from the high voltage generator 20.

The memory 23 stores various radiographing conditions such as tube voltage or a tube current in advance. The radiographing conditions are manually set by an operator through the touch panel 24. The radiation source control device 11 attempts to irradiate a subject with X-rays based on the tube voltage and a tube current-irradiation time product as the set radiographing conditions. Contrarily, when AEC detects that the radiation dose reaches a necessary and sufficient radiation dose, the AEC functions to stop the X-ray irradiation even when the radiation dose is equal to or less than the tube current-irradiation time product (irradiation time) in which the radiation source control device 11 attempts to perform irradiation. In order to end the X-ray irradiation before the AEC determines stopping of irradiation by reaching a target radiation dose and to prevent a radiation dose shortage from occurring, the maximum value of the tube current-irradiation time product (irradiation time is also possible) is set in the radiographing conditions of the X-ray source 10. In addition, it is preferable that the set tube current-irradiation time product be a value according to a radiographing region.

Figure 3:
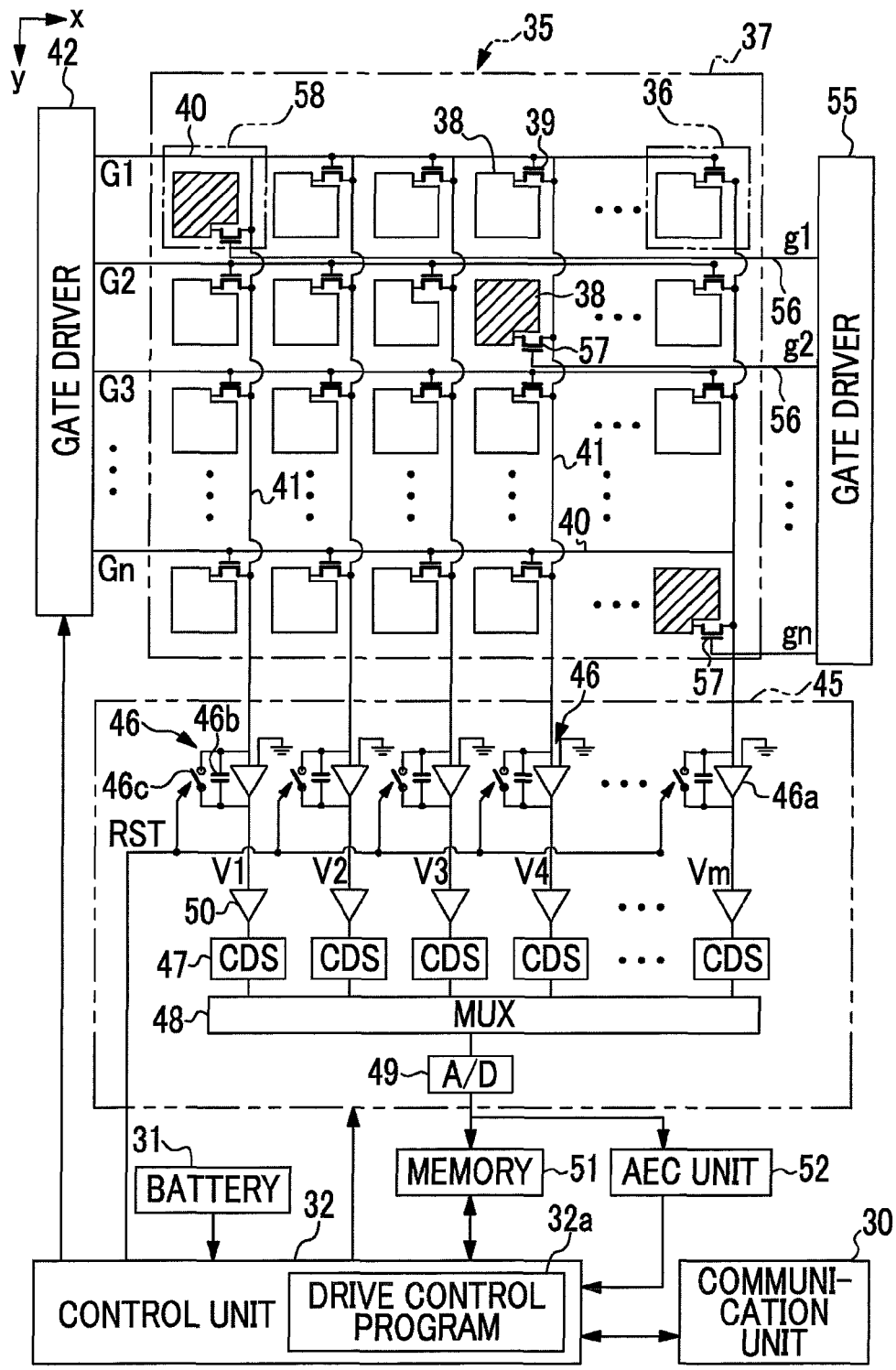
FIG. 3 is a block view showing an internal configuration of an electronic cassette.

An irradiation signal I/F 25 is connected with the electronic cassette 13 wirelessly in a case of defining X-ray irradiation stop timing based on an output of a detection pixel 58 of the electronic cassette 13 (refer to FIG. 3). In this case, when the warm-up start signal is received from the irradiation switch 12, the control unit 21 transmits an inquiry signal to the electronic cassette 13 through the irradiation signal I/F 25 wirelessly. When the electronic cassette 13 receives the inquiry signal, the electronic cassette 13 checks whether the cassette itself is capable of radiographing, and when it is determined that the cassette is in a capable state of radiographing, an irradiation permission signal is transmitted wirelessly. When the irradiation permission signal is received by the irradiation signal I/F 25, and further, the irradiation start signal is received from the irradiation switch 12, the control unit 21 starts power supply to the X-ray source 10 from the high voltage generator 20. In addition, when the irradiation continuation signal generated from the electronic cassette 13 is not received by the irradiation signal I/F 25 in a predetermined time (for example, multiple transmission period times of the irradiation continuation signal), the control unit 21 stops power supply to the X-ray source 10 from the high voltage generator 20 and stops the X-ray irradiation.

The electronic cassette 13 has an FPD 35 (refer to FIG. 3) and a portable case (not shown) which contains the FPD 35. The case of the electronic cassette 13 has an almost rectangular flat shape and the flat surface thereof is almost the same as a film cassette or an IP cassette (also referred to as a CR cassette) in size (a size according to international standard ISO 4090:2001). For this reason, the electronic cassette 13 can be attached to the existing radiographic stand for the film cassette and IP cassette.

Two electronic cassettes 13 are disposed for plural radiographic stands, for example, an upright radiographic stand 15 and a supine radiographic stand 16 in some rooms of radiographing rooms in which the X-ray radiographic system 2 is installed. The electronic cassette 13 is freely detachably set to holders 15a and 16a of the upright radiographic stand 15 and the supine radiographic stand 16 so as to be held in a posture in which a radiographing surface 37 of the FPD 35 (refer to FIG. 3) faces the X-ray source 10. The electronic cassette 13 is not set to the upright radiographic stand 15 and the supine radiographic stand 16, and can be used alone by being disposed above the bed on which a subject lies in a supine position or making a subject themself hold the cassette.

The console 14 is connected so as to be capable of communicating with the electronic cassette 13 in a wireless manner or a wired manner, and controls the operations of the electronic cassette 13 according to an input operation from an operator through an input device 14a such as a keyboard. Specifically, the console 14 controls power-on or power-off, and a mode switching to a waiting mode or a radiographing mode of the electronic cassette 13.

An X-ray image from the electronic cassette 13 is displayed on a display 14b of the console 14 and data of the X-ray image is stored in a storage device and a memory in the console 14, or a data storage device such as an image accumulation server connected to the console 14 via a network.

The console 14 receives an input of an inspection order including information of gender, age, a radiographing region, purpose of radiography of a patient and so on, and displays the inspection order on the display 14b. The inspection order is input from an exterior system which manages inspection information in relation to patient information or radiological inspection such as HIS (Hospital Information System) or RIS (Radiology Information System). Alternatively, the inspection order is manually input by an operator. The inspection order includes radiographing regions such as a head region, a chest region or a abdominal region and radiation directions such as front, side, oblique, PA (irradiating a subject with X-rays from the rear), and AP (irradiating a subject with X-rays from the front). The operator confirms the content of the inspection order on the display 14b and inputs the radiographing condition according to the content through an operation screen of the display 14b.

In FIG. 3, a communication unit 30 for communicating with the console 14 in a wireless manner or a wired manner, and a battery 31 are built in the electronic cassette 13. The communication unit 30 mediates various information including image data of the console 14 and a control unit 32 and transmission and reception of a signal. The battery 31 supplies power for operating each unit of the electronic cassette 13. The battery 31 is a relatively small battery to be used so as to be contained in the thin electronic cassette 13. In addition, the battery 31 can be detached outside from the electronic cassette 13 and set in an exclusive cradle to be charged. The battery 31 may be configured to be capable of wireless power feeding.

The communication unit 30 is connected with the console 14 by wire when the electronic cassette 13 and the console 14 cannot perform wireless communication with each other due to a low battery charge of the battery 31. When the communication unit 30 is connected to a cable from the console 14, the communication unit 30 is capable of wired communication with the console 14. At this time, power may be fed from the console 14 to the electronic cassette 13.

The control unit 32 collectively controls the driving of each unit in the electronic cassette 13 by executing a drive control program 32a stored in an internal memory. The control content of the drive control program 32a includes transmission of the irradiation continuation signal which will be described later.

The FPD 35 has a TFT active matrix substrate, and a radiographing surface 37 in which plural pixels 36 which accumulate charge according to a reached X-ray dose are arranged on the substrate. The plural pixels 36 are arranged in a two-dimensional matrix shape of n columns (x direction) and m rows (y direction) in a predetermined pitch.

The FPD 35 has a scintillator (fluorescent substance) which converts X-rays to visible light and is an indirect conversion type which photoelectrically converts the visible light converted by the scintillator with the pixels 36. The scintillator is made of CsI:Tl (thallium-activated cesium iodide), GOS ($Gd_2O_2S$:Tb, gadolinium oxysulfide) and the like and is disposed so as to face the entire surface of the radiographing surface 37 in which the pixels 36 are arranged. Here, the scintillator and the TFT active matrix substrate may be a PSS (penetration side sampling) type in which the scintillator and the substrate are disposed in order as seen from an incident side of X-rays, or conversely, may be an ISS (irradiation side sampling) type in which the substrate and the scintillator are disposed in order. In addition, a direct conversion type FPD using a conversion layer (amorphous selenium or the like) that directly converts the X-rays to charge without using the scintillator may be used.

The pixel 36 includes a photodiode 38 which is a photoelectric convert element generating charge (electron-hole pair) upon incidence of the visible light, a capacitor (not shown) which accumulates the charge generated by the photodiode 38, and a thin film transistor (TFT) 39.

The photodiode 38 has a configuration in which a semiconductor layer (for example, a PIN type) generating the charge is interposed between an upper electrode and a lower electrode. In the photodiode 38, the TFT 39 is connected to the lower electrode and a bias line is connected to the upper electrode. The bias lines equal to the number "n" of the columns (n columns) of the pixels 36 in the radiographing surface 37 are provided and are banded together as one wire connection. The wire connection is connected to bias power. A bias voltage is applied to the upper electrode of the photodiode 38 through the wire connection and the bias line from the bias power. The application of the bias voltage generates an electric field in the semiconductor layer. The charge (electron-hole pair) generated by the photoelectric conversion in the semiconductor layer is moved to the upper electrode and the lower electrode, one of which has positive polarity while the other has negative polarity. Thus, the charge is accumulated in the capacitor.

In the TFT 39, a gate electrode is connected to a scanning line 40, a source electrode is connected to a signal line 41, and a drain electrode is connected to the photodiode 38, respectively. The scanning lines 40 and the signal lines 41 are arranged in a lattice-like structure. The number of the scanning lines 40 equals to the number "n" of the columns (n columns) of the pixels 36 in the radiographing surface 37 and the number of the signal lines 41 equals to the number "m" of the rows (m rows) of the pixels 36. The scanning lines 40 are connected to a gate driver 42 and the signal lines 41 are connected to a signal processing circuit 45.

The gate driver 42 drives the TFT 39 and allows the TFT 39 to perform an accumulation operation in which the signal charge is accumulated in each of the pixels 36 according to the reached the X-ray dose, a read-out operation (actual reading) in which the signal charge is read out from the pixels 36, and a reset operation (idle reading). The control unit 32 controls start timing of each of the above-described various operations performed by the gate driver 42.

In the accumulation operation, the signal charge is accumulated in the pixels 36 while the TFTs 39 are turned off. In the read-out operation, the gate driver 42 sequentially generates gate pulses G1 to Gn to drive the TFTs 39 in the corresponding column at a time, and activate the scanning lines 40 on a column-by column basis so that the TFTs 39 connected to the scanning lines 40 are turned on by one column. When the TFTs 39 are turned on, the charge accumulated in the capacitors of the pixels 36 is read out by signal lines 41 and input to the signal processing circuit 45.

The signal processing circuit 45 is provided with integrating amplifiers 46, CDS circuits (CDS) 47, a multiplexer (MUX) 48, and an A/D converter (A/D) 49. The integrating amplifiers 46 are connected to the respective signal lines 41. Each integrating amplifier 46 includes an operational amplifier 46a and a capacitor 46b connected between input and output terminals of the operational amplifier 46a. The signal line 41 is connected to one input terminal of the operational amplifier 46a. The other input terminal of the operational amplifier 46a is connected to ground (GND). Reset switches 46c are paratactically connected to the capacitor 46b. Each of the integrating amplifiers 46 integrates the charge input from the corresponding signal line 41, and converts the charge into analog signals V1 to Vm to output the signals. The output terminal of the operational amplifier 46a of each row is connected to the MUX 48 through an amplifier 50 and the CDS 47. The output side of the MUX 48 is connected to the A/D 49.

The CDS 47 has a sample-and-hold circuit. In CDS 47, correlated double sampling is performed on the output voltage signal of the integrating amplifier 46 to remove noise and the output voltage signal of the integrating amplifier 46 is held in the sample-and-hold circuit for a predetermined period (sample-and-hold). The MUX 48 sequentially selects one CDS 47 from the parallel-connected CDS 47 of each row by an electronic switch based on a operation control signal from a shift register (not shown), and serially inputs the voltage signals V1 to Vm output from the selected CDS 47 to the A/D 49. The A/D 49 converts the input voltage signals V1 to Vm into digital voltage signals and outputs the digital voltage signals to a memory 51 or an AEC unit 52 in the electronic cassette 13. In addition, an amplifier may be connected between the MUX 48 and the A/D 49.

When the MUX 48 reads out the voltage signals V1 to Vm of one column from the integrating amplifier 46, the control unit 32 outputs a reset pulse RST to the integrating amplifier 46 and the reset switch 46c is turned on. Due to this, the signal charge of one column accumulated in the capacitor 46b is discharged and reset. The integrating amplifier 46 is reset, and then, one of the sample-and-hold circuits of the CDS 47 is held to perform sampling of a kTC noise component of the integrating amplifier 46 after a predetermined time has elapsed since the reset switch 46c is turned off again. Then, the gate driver 42 outputs the gate pulse for the next column to start the readout of the signal charge of the pixels 36 of the next column. Furthermore, the signal charge of the pixels 36 of the next column is held by the other sample—and hold circuit of the CDS 47 after a predetermined time has elapsed since the gate pulse is output. The above operations are sequentially repeated to read out the signal charge of the pixels 36 of all the columns.

When the readout of all the columns is completed, image data representing an X-ray image of one frame is recorded in the memory 51. The image data is read out from the memory 51 and output to the console 14 through the communication unit 30. In this manner, the X-ray image of the subject is detected.

Dark charge is generated in the semiconductor layer of the photodiode 38 regardless of presence or absence of the X-ray incidence. The dark charge is accumulated in the capacitor of the pixel 36 due to the application of the bias voltage. The dark charge generated in the pixel 36 is a noise component in the image data, so the reset operation is performed in a predetermined time interval to remove the dark charge. The reset operation refers to releasing the dark charge generated in the pixel 36 through the signal line 41.

For example, the reset operation of the pixels 36 is performed in a sequential resetting method in which each column of the pixels 36 is reset. In the sequential resetting method, the gate driver 42 generates the gate pulses G1 to Gn sequentially to the scanning lines 40, similar to the read-out operation of the signal charge. Thereby, the TFTs 39 of the pixels 36 are turned on, on a column-by-column basis. While the TFTs 39 are turned on, the dark charge flows from the pixels 36 to the capacitors 46b of the integrating amplifiers 46 through the signal lines 41. In the reset operation, unlike the read-out operation, the charge accumulated in the capacitor 46b is not read out by the MUX 48. Instead, the reset pulse RST is output from the control unit 32 to turn on the reset switch 46c by synchronizing with the generation of the respective gate pulses G1 to Gn, and thereby the charge accumulated in the capacitor 46b is discharged to reset the integrating amplifier 46.

Instead of the sequential resetting method, a parallel resetting method or an all-pixel resetting method may be used. In the parallel resetting method, plural columns of the arrangement pixels are set as a group and the sequential resetting is performed in the group. The dark charge of columns of the number of the groups is released simultaneously. In the all-pixel resetting method, a gate pulse is input to every column to release the dark charge of all the pixels at a time. The parallel resetting method or the all-pixel resetting method can enhance the speed of the reset operation.

The FPD 35 has plural detection pixels 58 to which TFTs 57 driven by a separate gate driver 55 and separate scanning lines 56 from the normal pixel 36 are connected in the same radiographing surface 37, in addition to the normal pixels 36 to which the TFTs 39 driven by the above-described gate driver 42 and the scanning lines 40 are connected. The TFTs 57 are turned on by the gate pluses G1 to Gn from the gate driver 55. The detection pixel 58 has the same basic configuration such as the photodiode 38 as that of the pixel 36 but only has a different driving source. The accumulated charge can be read out from the signal line 41 independent of the pixel 36. In the reset operation and the read-out operation, the operation of the normal pixel 36 is done and then, in the same manner, the gate driver 55 generates the gate pluses G1 to Gn to perform the reset operation or the read-out operation of the detection pixel 58. Alternatively, the reset operation or the read-out operation of the pixel 36 and the detection pixel 58 in the same column is simultaneously performed by synchronizing with the operation of the gate driver 42. The detection pixel 58 is a pixel used to detect the X-ray dose reaching the radiographing surface 37 and functions as an AEC sensor. The detection pixel 58 occupies several ppm to several % of the pixels 36 in the radiographing surface 37.

Figure 4:
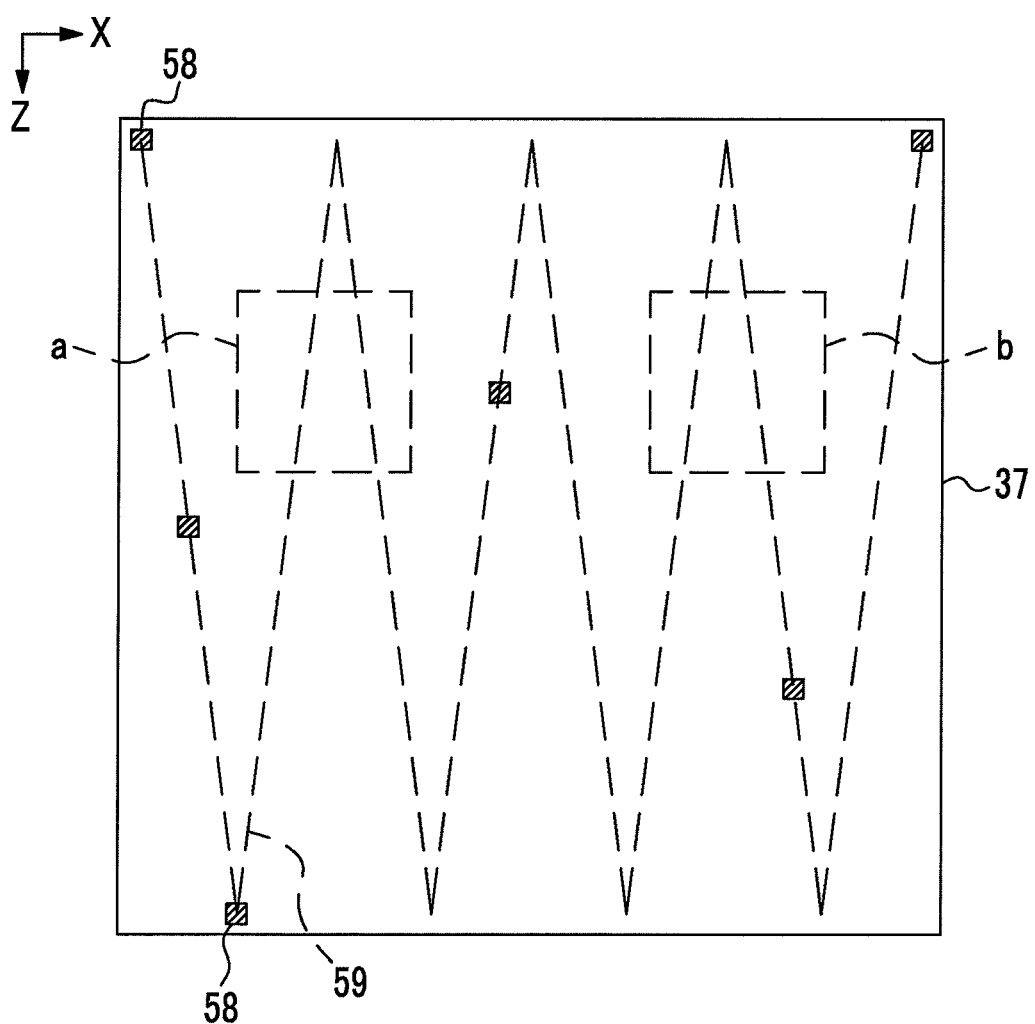
FIG. 4 is a view for describing an arrangement of detection pixels.

As shown in FIG. 4, the detection pixels 58 are not locally placed on the radiographing surface 37 and are provided along a wave-like trace 59 represented by a dotted line that is bilaterally symmetric with respect to the center of the radiographing surface 37 so as to be evenly dispersed on the radiographing surface 37. The detection pixel 58 is provided in the row of the pixel 36 connected to the same signal line 41 one by one and the row in which the detection pixel 58 is provided is provided with interposing of, for example, two or three rows in which the detection pixels 58 are not provided. The position of the detection pixel 58 is known at the time of manufacturing the FPD 35, and the FPD 35 stores the positions (coordinates) of all the detection pixels 58 in a non-volatile memory (not shown) in advance. Contrary to the embodiment, the detection pixels 58 may be locally and intensively placed and the arrangement of the detection pixels 58 can be appropriately changed. For example, the detection pixels 58 may be intensively arranged on a chest wall side in a mammography device that radiographs a breast.

When the gate driver 55 outputs the gate pluses to turn on the TFT 57, the signal charge generated by the detection pixel 58 is read out by the signal line 41. Due to a different driving source of the pixel 36, the signal charge of the detection pixel 58 can be read out even in the accumulation operation in which the pixel 36 in the same row turns on the TFT 39, and the signal charge is accumulated. At this time, charge generated by the detection pixel 58 flows into the capacitor 46b of the integrating amplifier 46 on the signal line 41 to which the detection pixel 58 is connected. At the time of the accumulation operation of the pixel 36, the charge from the detection pixel 58 accumulated in the integrating amplifier 46 by turning on the TFT 57 is output to the A/D 49 in a predetermined sampling period.

Circuits (not shown) which perform various image processes such as offset correction, sensitivity correction and defect correction on the data of the X-ray image in the memory 51 is provided in the control unit 32. The offset correction circuit subtracts an offset correction image acquired from the FPD without irradiation of X-rays from the X-ray image by a pixel unit and removes fixed pattern noise caused by an individual difference of the signal processing circuit 45 or a radiographic environment.

The sensitivity correction circuit is also referred to as a gain correction circuit, and corrects unevenness in sensitivity of the photodiode 38 of each pixel 36 or unevenness in output properties of the signal processing circuit 45. The sensitivity correction is performed based on sensitivity correction data generated from the image subtracting the offset correction image from an image obtained by irradiation of X-rays of a predetermined dose without any subject. When the irradiation of X-rays of a predetermined dose is performed without any subject, the sensitivity correction data has a coefficient for each pixel correcting a shift from a reference value so that output of each pixel becomes uniformly same by multiplying the X-ray image after the offset correction. For example, when output of a pixel A is 1 which is a reference value, and output of a pixel B is 0.8, a coefficient of the pixel B is 1.25 (1/0.8=1.25).

The defect correction circuit performs linear interpolation of a pixel value of a defect pixel with a pixel value of a peripheral normal pixel based on defect pixel information added in shipping. In addition, the pixel value of the detection pixel 58 in a lighting field used in radiation dose detection of AEC is interpolated in the same manner.

While the offset correction image and the sensitivity correction data are acquired, for example, at the time of shipping the electronic cassette 13, a serviceman of a manufacturer or an operator acquires the offset correction image and the sensitivity correction data in periodic maintenance or in opening time of a hospital and records the offset correction image and the sensitivity correction data in the internal memory of the control unit 32 to be read out in correction. The various image processing circuits are provided in the console 14 and various image processes may be performed by the console 14.

The AEC unit 52 is drive-controlled by the control unit 32. The AEC unit 52 acquires a digital voltage signal (hereinafter, referred to as a radiation dose detection signal) from the signal line 41 to which the detection pixel 58 is connected from the A/D 49 and AEC is performed based on the acquired radiation dose detection signal.

Figure 5:
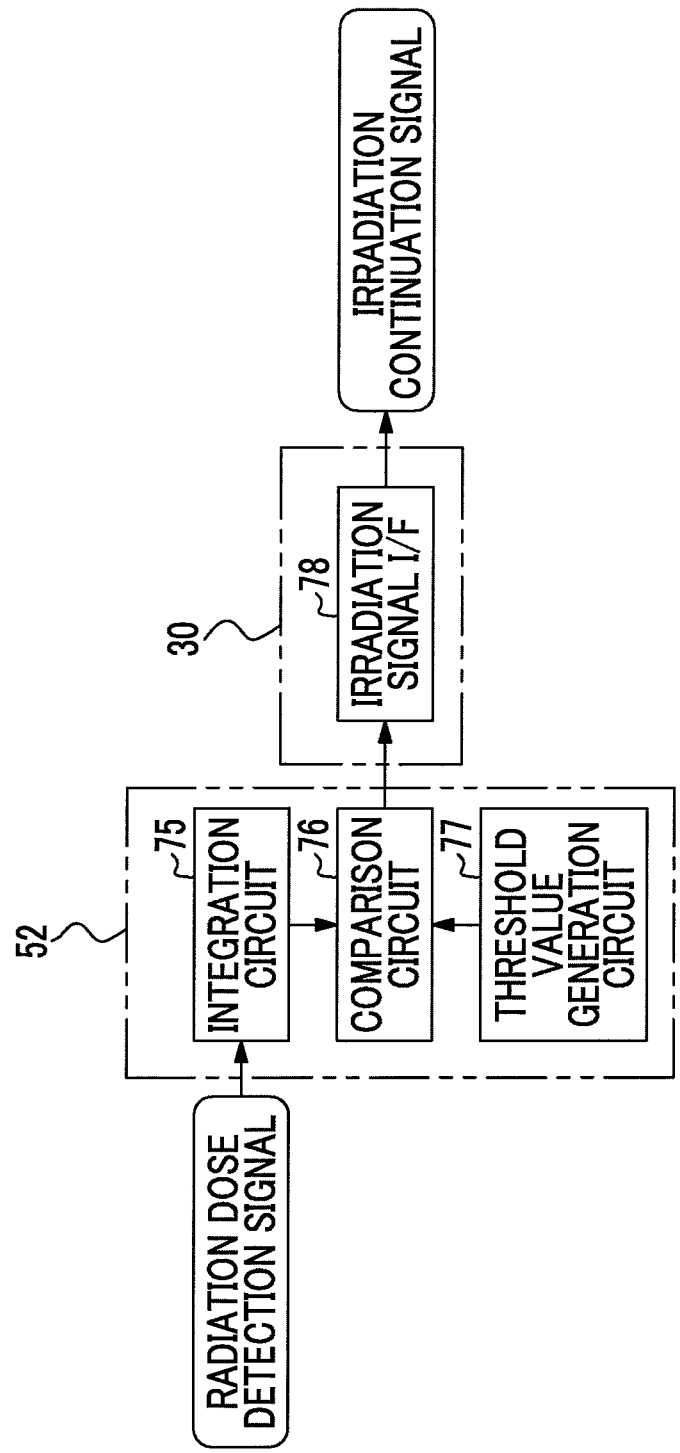
FIG. 5 is a block view showing internal configurations of an AEC unit and a communication unit of the electronic cassette.

In FIG. 5, the AEC unit 52 has an integration circuit 75, a comparison circuit 76 (an embodiment of an automatic exposure control unit and an irradiation stop determination unit), and a threshold value generation circuit 77. The integration circuit 75 integrates an average value, the maximum value, a mode value or a total value of the radiation dose detection signals from the detection pixels 58 in a lighting field. When the waiting mode in which the reset operation is repeated is switched to a radiographing mode in which the accumulation operation is started, the comparison circuit 76 starts the monitoring of the integrated value of the radiation dose detection signal from the integration circuit 75. Then, the comparison circuit 76 compares the integrated value and an irradiation stop threshold value given from the threshold value generation circuit 77 with an appropriate timing. The comparison circuit 76 starts output of the irradiation continuation signal simultaneously with the start of the monitoring of the integrated value, and while the integrated value reaches the threshold value, the comparison circuit 76 continuously outputs the irradiation continuation signal in a predetermined period. When it is determined that the integrated value reaches the threshold value, the comparison circuit 76 stops the output of the irradiation continuation signal.

An irradiation signal I/F 78 is provided in the communication unit 30. The irradiation signal I/F 25 of the radiation source control device 11 is connected to the irradiation signal I/F 78 wirelessly. The irradiation signal I/F 78 performs reception of the inquiry signal, transmission of the irradiation permission signal to the inquiry signal, reception of the irradiation start signal, and output of the comparison circuit 76, that is, transmission of the irradiation continuation signal.

As for the wireless communication method between the irradiation signal I/F 25 of the radiation source control device 11 and the irradiation signal I/F 78 of the electronic cassette 13, ad-hoc communication is used. The ad-hoc communication refers to direct wireless communication between wireless communication devices. For this reason, a delay (lag) of data communication does not easily occur and an average delay time of data communication is reduced in comparison with infrastructure communication to perform communication of medical equipment other than the X-ray radiographic system 2, and various data communication such as electronic medical charts, medical reports, and accounting data through a wireless access point or a switching device such as an in-hospital LAN or hub. Therefore, the communication speed of the ad-hoc communication is faster than that of the infrastructure communication.

The radiation source control device 11 is often placed in a radiographing room. Due to this, when AEC signal communication including the irradiation continuation signal between the radiation source control device 11 and the electronic cassette 13 is ad-hoc communication, a distance between the radiation source control device 11 and the electronic cassette 13 is close and radio waves easily arrive so that stable communication can be performed and high-speed communication can be implemented without the delay of data communication.

As for the wireless communication method between the irradiation signal I/F 25 and the irradiation signal I/F 78, for example, an optical beacon represented as infrared data communication such as IrDA or a radio beacon is preferably employed. Since the bit number of an exchange signal is relatively small, the communication method is also simple, and the delay does not easily occur, the optical beacon and the radio beacon are suitable for the AEC signal communication to immediately stop the X-ray irradiation in case where the radiation dose reaches the target radiation dose.

As shown in FIG. 6, it is possible to set radiographing conditions in each radiographing region by the input device 14a in the console 14. The irradiation stop threshold value to determine X-ray irradiation stop by comparing the tube voltage, the tube current, the lighting field of the detection pixel 58 and the integrated value of the radiation dose detection signal of the detection pixel 58 is stored in the radiographing conditions. The radiographing condition information is stored in the storage device and a radiographing condition corresponding to a radiographing region designated by the input device 14a is read out by the storage device to provide the information to the electronic cassette 13. As for the radiographing conditions of the radiation source control device 11, an operator manually sets the same radiographing conditions with reference to the radiographing conditions of the console 14.

The lighting field which shows an area of the detection pixel 58 using AEC, is an interest area which is an area to be paid attention when diagnosing, and a region obtained by stabilizing the radiation dose detection signal is set to every radiographing region. For example, when the radiographing region is a chest region, the right and left lung fields are set as a lighting field as represented by a and b surrounded by a dotted line in FIG. 4. The lighting field is shown by xy coordinates and when the lighting field is a rectangle, for example, two xy coordinates connected by a diagonal line are stored as shown in the example. The XY coordinates correspond to positions in the radiographing surface 37 of the pixel 36 also including the detection pixel 58 of the electronic cassette 13, a direction parallel to the scanning line 40 is set as an x axis and a direction parallel to the signal line 41 is set as a y axis to express the coordinate of the upper left pixel 36 in the original point (0,0).

Figure 7:
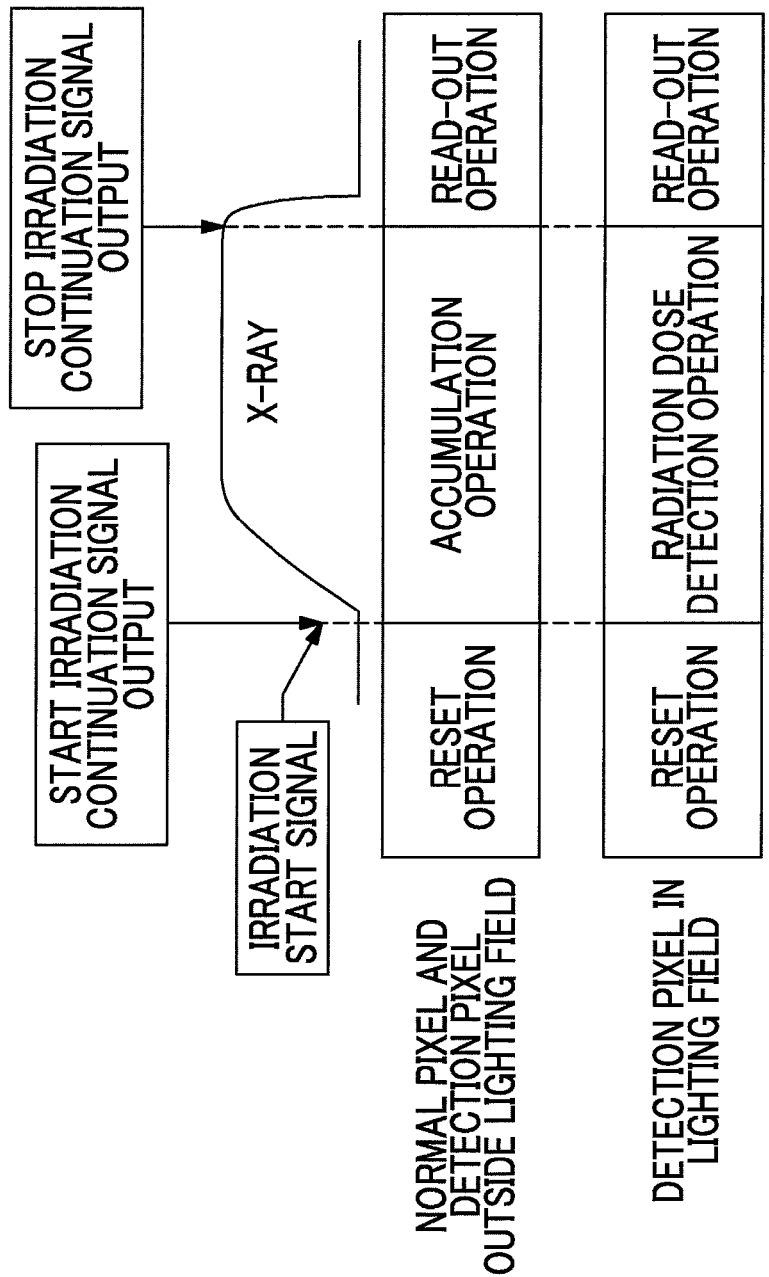
FIG. 7 is a view showing a transition of an FPD operation in X-ray radiography.

In FIG. 7, before the radiographing, the FPD 35 is operated in a waiting mode in which the reset operation is repeated with respect to both the pixel 36 and the detection and pixel 58. When the irradiation signal I/F 78 receives the irradiation start signal, the control unit 32 controls the FPD 35 to end the reset operation and start the accumulation operation so that the waiting mode is switched to a radiographing mode. However, only for the detection pixel 58 in the lighting field set in the radiographing conditions, a radiation dose detection operation to output the radiation dose detection signal by turning on the TFT 57 is started.

In the comparison circuit 76 of the AEC unit 52, the monitoring of the integrated value of the radiation dose detection signal from the integration circuit 75 is started simultaneously with starting the output of the irradiation continuation signal. While the irradiation continuation signal is transmitted from the irradiation signal I/F 78 to the irradiation signal I/F 25 wirelessly, and the irradiation signal I/F 25 receives the irradiation continuation signal, the X-ray irradiation by the X-ray source 10 continues. Then, the integrated value of the radiation dose detection signal reaches the irradiation stop threshold value, and the output of the irradiation continuation signal from the comparison circuit 76 is stopped. Due to this, the wireless transmission of the irradiation continuation signal from the irradiation signal I/F 78 is paused so that the irradiation signal I/F 25 does not receive the irradiation continuation signal. After a predetermined time has elapsed since the irradiation continuation signal is not received, the X-ray irradiation by the X-ray source 10 is stopped. At this time, the control unit 32 makes transition of the operation of the FPD 35 from the accumulation operation to the read-out operation, irrespective of the pixel 36, the detection pixel 58 outside the lighting field, and the detection pixel 58 in the lighting field. Therefore, a single radiography is ended. The FPD 35 returns to the waiting mode. In addition, the pixel value of the detection pixel 58 in the lighting field obtained from the read-out operation is not employed as image data and the pixel value interpolated by the defect correction circuit is employed.

Figure 8:
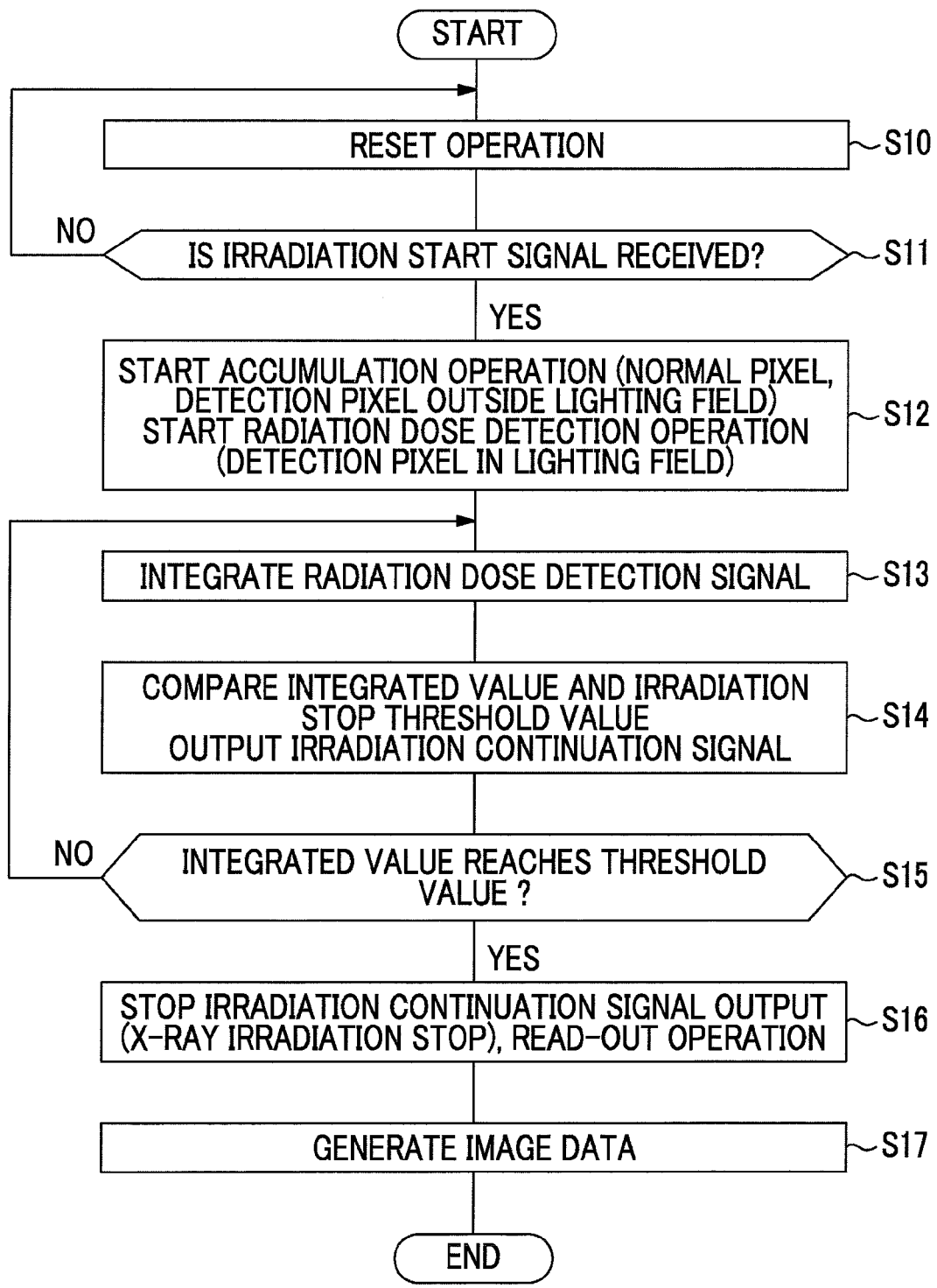
FIG. 8 is a flowchart showing a flow of an X-ray radiographic process.

Next, a procedure in a case of performing X-ray radiography in the X-ray radiographic system 2 will be described with reference to the flowchart in FIG. 8. First, a subject is allowed to stand at a predetermined position in front of the upright radiographic stand 15 or lie on the supine radiographic stand 16, the height or the horizontal position of the electronic cassette 13 is set to any one of the upright and supine radiographic stands 15 and 16 is adjusted so as to match a radiographing region of the subject and the position. In addition, the height or the horizontal position of the X-ray source 10, the size of an irradiation field are adjusted according to the position of the electronic cassette 13 and the size of the radiographing region. Next, the radiographing conditions of the radiation source control device 11 and the console 14 are set.

In Step (S10), in the waiting mode before X-ray radiography, the control unit 32 controls the FPD 35 to repeat the reset operation. After the irradiation switch 12 is pressed one stage, and the inquiry signal and the irradiation permission signal are exchanged between the irradiation signal I/Fs 25 and 78, the irradiation switch 12 is pressed two stages and the irradiation start signal is output from the radiation source control device 11. When the irradiation signal I/F 78 receives the signal (YES in S11), the pixel 36 and the detection pixel 58 outside the lighting field makes the transition from the reset operation to the accumulation operation to be switched to a radiographing mode. On the other hand, the TFT 57 is turned on and the detection pixel 58 in the lighting field set in the radiographing conditions makes the transition to the radiation dose detection operation (S12).

The X-ray irradiation by the X-ray source 10 is started by pressing the irradiation switch 12 two stages. The charge generated therefrom is accumulated in the photodiode 38 in a case of the pixel 36 and the detection pixel 58 outside the lighting field, and the charge flows into the integrating amplifier 46 through the signal line 41 in a predetermined sampling period to be output from the integrating amplifier 46 to the A/D 49 and the AEC unit 52 as a radiation dose detection signal in a case of the detection pixel 58 in the lighting field.

The radiation dose detection signal from the detection pixel 58 in the lighting field is output to the integration circuit 75 of the AEC unit 52, and accumulated in the integration circuit 75 (S13). The threshold value generation circuit 77 generates the irradiation stop threshold value given by the console 14 and outputs the value to the comparison circuit 76. The comparison circuit 76 compares the integrated value of the radiation dose detection signal from the integration circuit 75 and the irradiation stop threshold value of the threshold value generation circuit 77 and simultaneously outputs the irradiation continuation signal in a predetermined period (S14). The irradiation continuation signal is transmitted to the irradiation signal I/F 25 of the radiation source control device 11 through the irradiation signal I/F 78 wirelessly.

When the integrated value of the radiation dose detection signal reaches the threshold value (YES in S15), the output of the irradiation continuation signal from the comparison circuit 76 is stopped. In addition, the operation of the FPD 35 transitions from the accumulation operation to the read-out operation (S16).

When the wireless transmission of the irradiation continuation signal is paused in the irradiation signal I/F 25 in a predetermined time, the control unit 21 stops power supply to the X-ray source 10 from the high voltage generator 20 to stop X-ray irradiation in the radiation source control device 11.

The various image processing circuits of the control unit 32 perform various image processes on the X-ray image data output to the memory 51 in the read-out operation and one piece of the X-ray image is generated in this manner (S17). The X-ray image is transmitted to the console 14 through the communication unit 30 by wire or wireless and displayed on the display 14b to be provided for diagnosis.

As described above, according to the present invention, until the integrated value of the radiation dose detection signal reaches the irradiation stop threshold value and the AEC unit 52 determines to stop X-ray irradiation, the irradiation continuation signal is continuously transmitted from the electronic cassette 13 to the radiation source control device 11. When the integrated value reaches the threshold value, the transmission of the irradiation continuation signal is stopped and when the reception of the irradiation continuation signal to the radiation source control device 11 is paused, X-ray irradiation is stopped. Therefore, even when communication failure is generated between irradiation signal I/Fs 25 and 78 during the X-ray irradiation and the signal exchange is not possible, the X-ray irradiation can be safely stopped.

In the related art, when the integrated value reaches the threshold value, the irradiation stop signal is transmitted from the electronic cassette 13 to the radiation source control device 11 and the radiation source control device 11 receives the irradiation stop signal so that the X-ray irradiation is stopped. For this reason, in a situation in which the irradiation stop signal cannot be transmitted and received between the electronic cassette 13 and the radiation source control device 11, even when the time to stop the X-ray irradiation elapses, the X-ray irradiation is continuously performed and there is concern that a patient may be exposed to unnecessary radiation. Contrarily, in the present invention, when the reception of the irradiation continuation signal is paused, the X-ray irradiation is stopped. Therefore, there may be a radiation dose shortage. However, at least, there is no concern that a patient may be exposed to unnecessary radiation.

Since communication failure easily occurs in wireless communication in comparison with wired communication, the present invention is applied to wireless communication of an AEC signal including the irradiation continuation signal as in the embodiment, so that an excellent effect can be exhibited. Since communication failure also occurs in wired communication due to cable disconnection and connection failure, the present invention may be applied to wired communication of the AEC signal including the irradiation continuation signal.

Figure 9:
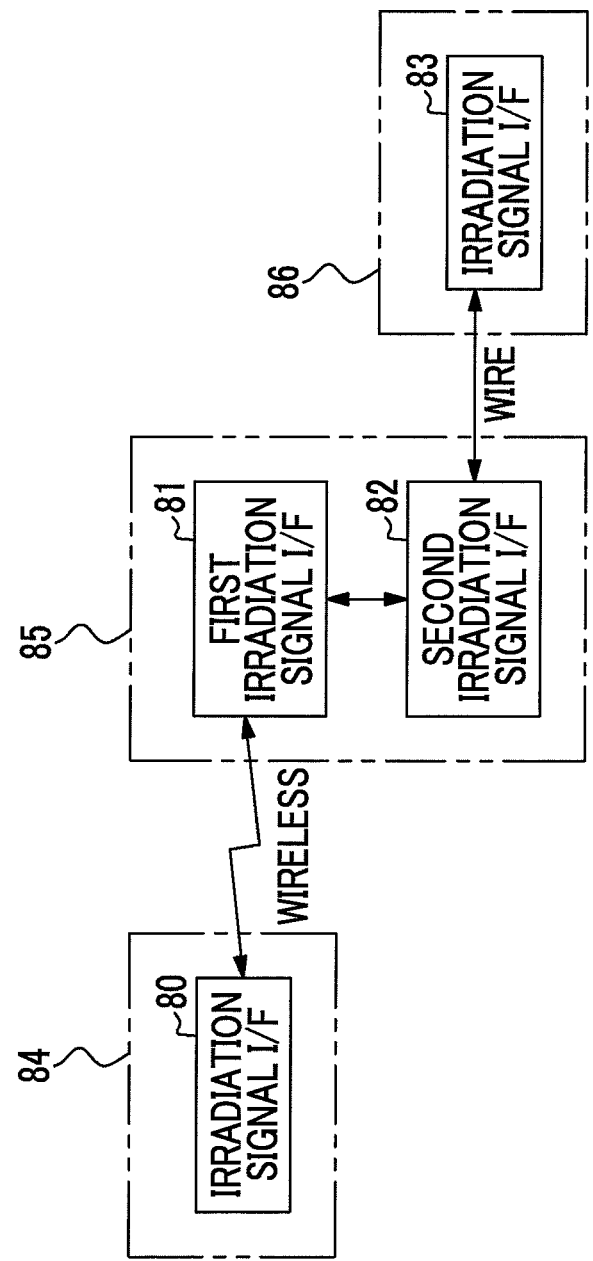
FIG. 9 is a block diagram showing a state in which an irradiation continuation signal is transmitted from the electronic cassette to the radiation source control device through the console.

In the above embodiment, the exchange of the irradiation continuation signal between the radiation source control device and the electronic cassette is described. However, the exchange of the irradiation continuation signal may be performed through a console. For example, as shown in FIG. 9, an electronic cassette 84, a console 85 and a radiation source control device 86 in which irradiation signal I/Fs 80, 81, 82 and 83 performing wireless or wired communication of the AEC signal including the irradiation continuation signal is respectively provided may be used.

The irradiation signal I/F 80 of the electronic cassette 84 performs wireless communication of the signal as the irradiation signal I/F 78 in the above embodiment except that an opposite side to exchange the signal is not the radiation source control device 86 but the first irradiation signal I/F 81 of the console 85. The irradiation signal I/F 83 of the radiation source control device 86 is connected with the second irradiation signal I/F 82 of the console 85 by wire to perform wired communication of the signal. While the first irradiation signal I/F 81 demodulates the signal received from the irradiation signal I/F 80 of the electronic cassette 84 wirelessly to transfer the demodulated signal to the second irradiation signal I/F 82, the signal from the irradiation signal I/F 83 of the radiation source control device 86 that the second irradiation signal I/F 82 receives by wire is modulated and transmitted to the irradiation signal I/F 80 of the electronic cassette 84 wirelessly.

In this case, when the irradiation continuation signal is exchanged between the electronic cassette 84 and the console 85 as in the embodiment and the reception of the irradiation continuation signal by the console 85 is paused, the irradiation stop signal to stop the X-ray irradiation is transmitted to the irradiation signal I/F 83 of the radiation source control device 86 from the second irradiation signal I/F 82. The radiation source control device 86 receives the irradiation stop signal to stop the X-ray irradiation. Then, an AEC control device that is exclusive to an AEC process without a console function is provided separately from the console 85, the irradiation continuation signal is exchanged between the electronic cassette 84 and the AEC control device, and the irradiation stop signal is exchanged between the AEC control device and the radiation source control device 86.

In addition, since the console 85 is connected with the radiation source control device 86 by wire, there is a very low possibility of communication failure. However, when communication failure occurs by any possibility, the irradiation stop signal cannot be transmitted or received. Moreover, since the console 85 is configured by a personal computer, it can be considered that an OS freezes and a communication function does not work. Then, the irradiation stop signal is not exchanged between the console 85 and the radiation source control device 86, and the exchange of the irradiation continuation signal is more preferable as between the electronic cassette 84 and the console 85. In this case, when the irradiation continuation signal is transmitted from the second irradiation signal I/F 82 in the same manner and the reception of the irradiation continuation signal by the first irradiation signal I/F 81 is paused during the reception of the irradiation continuation signal by the first irradiation signal I/F 81, the transmission of the irradiation continuation signal from the second irradiation signal I/F 82 is also stopped. Accordingly, even when communication failure occurs between the electronic cassette 84 and the console 85, or between the console 85 and the radiation source control device 86, it is possible to safely stop the X-ray irradiation.

In the above embodiment, a case in which the radiographing room is a single room is exemplified. However, plural radiographing rooms are provided considering the number of patients and waiting time for a medical examination in a relatively large hospital and the respective radiographing rooms are often adjacent with an interposing wall therebetween. Therefore, as in the embodiment, when the wireless communication of the AEC signal including the irradiation continuation signal is performed, there is concern that interference may occur between the systems of adjacent rooms.

Figure 10:
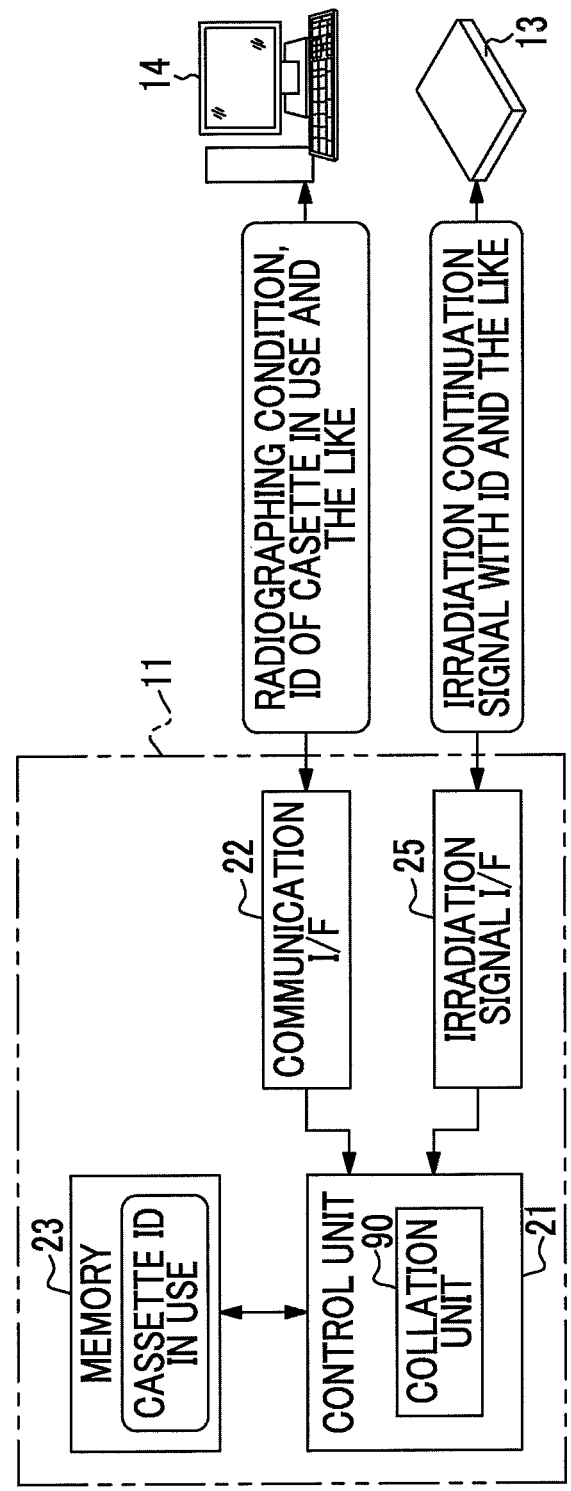
FIG. 10 is a view showing a state in which an ID of the electronic cassette in use is provided to the irradiation continuation signal to be collated by the radiation source control device.

As shown in FIG. 10, an ID of the electronic cassette 13 in use is stored in the memory 23 (an embodiment of a storage unit) of the radiation source control device 11 in advance, and the ID is embedded in the irradiation continuation signal transmitted from the electronic cassette 13. In addition, a collation unit 90 (an embodiment of a collation unit) is provided in the control unit 21 and the ID stored in the memory 23 is collated with an ID embedded in the signal received by the irradiation signal I/F 25 in the collation unit 90 of the radiation source control device 11. Then, the reception of a collated signal is permitted and the reception of an uncollated signal is refused. The ID of the electronic cassette 13 in use is input by the input device 14a of the console 14 before starting radiography and acquired through the communication I/F 22. It is possible to reliably prevent signal interference. Here, the irradiation switch 12 and the touch panel 24 are not shown in FIG. 10.

When communication failure occurs between the I/Fs exchanging the irradiation continuation signal during the X-ray irradiation, even before an accumulated radiation dose of the X-ray reaches the target radiation dose, the X-ray irradiation is stopped and a radiation dose shortage is caused. Therefore, radiography needs to be performed again in this case. However, since an operator cannot distinguish whether the X-ray irradiation is normally stopped by AEC or whether the X-ray irradiation is unavoidably stopped due to communication failure at the spot, the operator recognizes that radiography needs to be performed again after the interpretation of the X-ray image or there is concern of oversight without recognition of the radiation dose shortage depending on the case. In addition, when the X-ray irradiation is stopped due to communication failure, a chance to allow the FPD 35 to perform the read-out operation is lost.

It is preferable that the purport when the X-ray irradiation is stopped due to communication failure is displayed as a warning to the operator. Specifically, as shown in S20 of FIG. 11, while the comparison circuit 76 of the AEC unit 52 compares the integrated value of the radiation dose detection signal and the irradiation stop threshold value, the integrated value on which sampling is performed in the previous time and the integrated value on which sampling is performed in this time are compared. The integrated value in the previous time is sequentially updated and stored in the internal memory of the comparison circuit 76. While the X-ray irradiation continues, the integrated value in this time is larger than the integrated value in the previous time. When the X-ray irradiation is stopped, the integrated value is not increased, and the integrated value in the previous time and the integrated value in this time become the same. When the integrated value in the previous time and the integrated value in this time become the same before the integrated value reaches the threshold value (YES in S20), it is determined that the X-ray irradiation is stopped due to communication failure.

Figure 11:
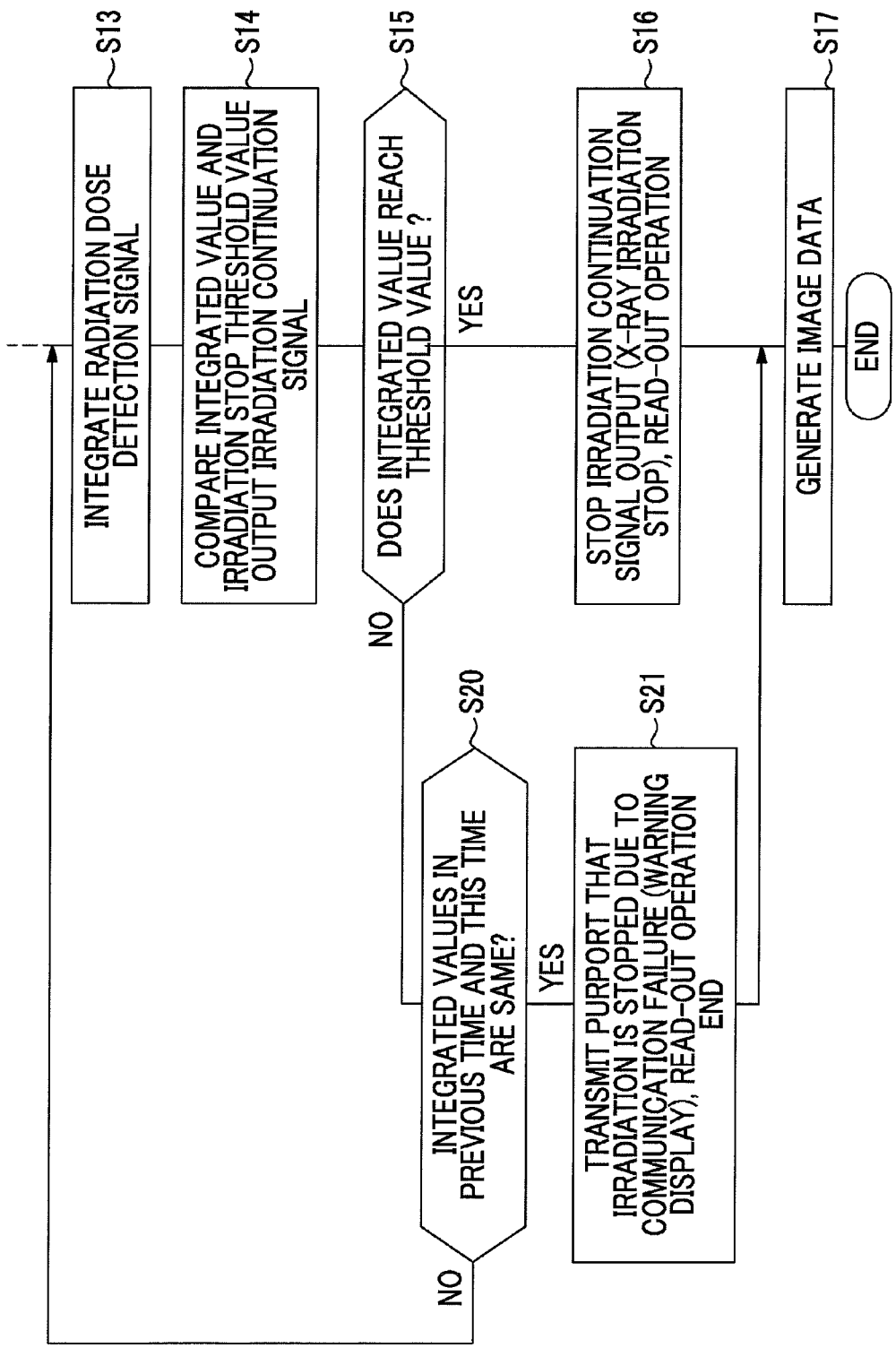
FIG. 11 is a flowchart showing a state in which the purport that X-ray irradiation is stopped due to communication failure is displayed as warning.
Figure 12:
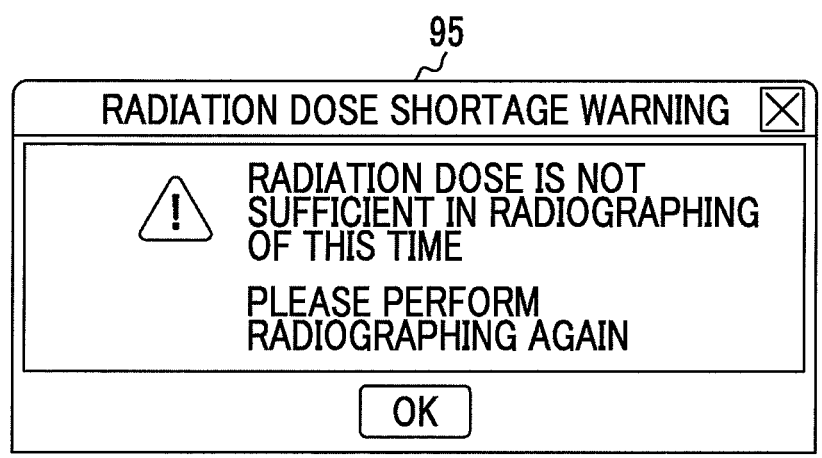
FIG. 12 is a view showing an example of the warning display.

When it is determined that the X-ray irradiation is stopped due to communication failure in the comparison circuit 76, the control unit 32 of the electronic cassette 13 makes the FPD 35 perform the read-out operation and transmits a signal of the purport that the X-ray irradiation is stopped due to communication failure to the console 14 through the communication unit 30 (S21). The console 14 receives the signal of the purport and for example, a warning display window 95 shown in FIG. 12 is displayed on the display 14*b*. The operator is notified of the end of radiography due to a radiation dose shortage and the necessity of radiographing again, which performs radiographing again in the same radiographing conditions. In addition, a beep sound may be generated from a speaker or a warning lamp may be prepared and lighted. In this case, a part of the control unit 32 and a part of the console 14 configure a warning display unit. Moreover, a warning display may be provided in the electronic cassette 13 itself. In FIG. 11, the same step as in FIG. 8 is denoted by the same reference numeral and steps before S13 are omitted.

Figure 13:
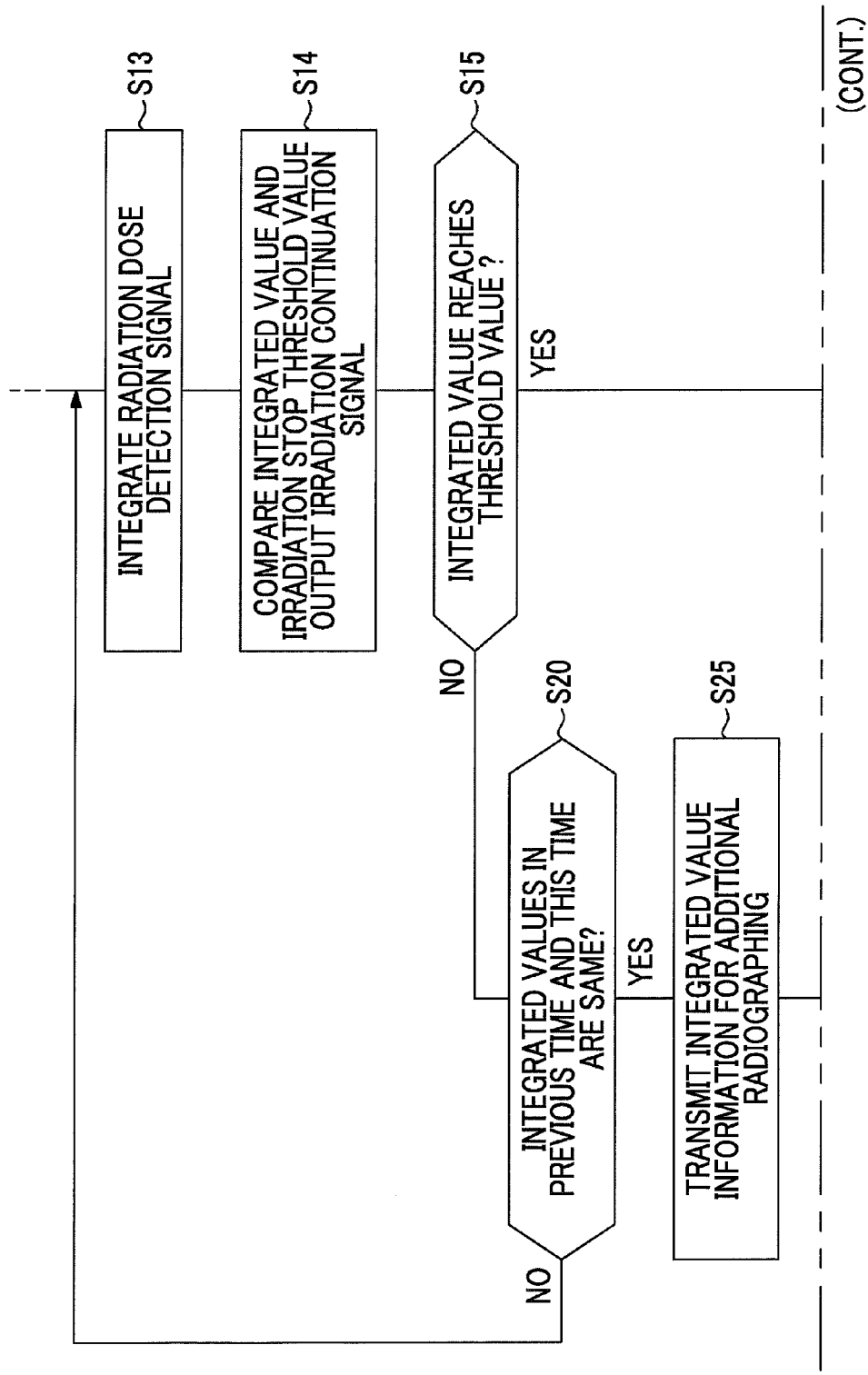
FIG. 13 is a flowchart showing a state in which radiography which makes up for a radiation dose shortage is performed when X-ray irradiation is stopped due to communication failure.

Alternatively, when the X-ray irradiation is stopped due to communication failure, radiography which makes up for the radiation dose shortage may be continuously and automatically performed. Even in this case, as shown in FIG. 13, it is determined that the X-ray irradiation is stopped due to communication failure in the comparison circuit 76 as in the case of warning display (YES in S20), and further, the information of the integrated value of the radiation dose detection signal is transmitted to the console 14 at that time (S25). In this case, the FPD 35 makes the accumulation operation and the radiation dose detection operation proceed. In FIG. 13, the same step as in FIG. 8 is denoted by the same reference numeral and steps before S13 are omitted, as in FIG. 11.

The console 14 obtains the difference between the integrated value of the radiation dose detection signal transmitted from the electronic cassette 13 and the irradiation stop threshold value set in the radiographing conditions to calculate a radiation dose shortage. Then, a tube current-irradiation time product or the relationship of irradiation time and a radiation dose is stored in every radiographing region (tube voltage) in advance, and a radiographing condition (tube current-irradiation time product or irradiation time) which makes up for the radiation dose shortage calculated based on the tube current-irradiation time product or the relationship of irradiation time and a radiation dose is obtained. The obtained radiographing condition is transmitted to the communication I/F 22 of the radiation source control device 11. The control unit 21 of the radiation source control device 11 controls driving of the high voltage generator 20 and X-ray irradiation is additionally performed by the radiographing condition received through the communication I/F 22.

In the electronic cassette 13, monitoring of the integrated value of the radiation dose detection signal from the integration circuit 75 by the comparison circuit 76 proceeds (S26). When the X-ray irradiation by the radiographing condition which makes up for the radiation dose shortage is stopped, the integrated value in the previous time and the integrated value in this time become the same again (YES in S27). When the integrated value in the previous time and the integrated value in this time become the same, the control unit 32 makes the FPD 35 perform the read-out operation (S28). When the X-ray irradiation is stopped due to communication failure and the radiation dose is not sufficient, radiography which makes up for the radiation dose shortage is immediately performed so that a labor of radiographing again can be saved. Here, the AEC unit determines that the X-ray irradiation is stopped. However, an irradiation stop determination unit may be provided separately from the AEC unit.

In the above embodiment, the electronic cassette 13 in which the AEC signal is exchanged by the exclusive irradiation signal I/F 78 is exemplified. In this case, when the AEC signal is exchanged, other signals and data such as radiographing conditions and image data are not exchanged and the function of the communication unit 30 other than the irradiation signal I/F 78 is temporarily stopped so that power saving may be achieved. Contrarily, when the AEC signal is not exchanged, the function of the irradiation signal I/F 78 may be stopped.

In addition, the communication function of the AEC signal and other signals or data may be performed by one I/F. Costs are low in comparison to a case of separately providing an I/F with each having separate communication functions. In this case, the communication I/F can change a communication speed. When the AEC signal is transmitted, an exposure dose of a subject is related. Therefore, it is preferable to perform high speed communication. When other signals or data is transmitted, urgency is lower in comparison with the case of the AEC signal transmission. Therefore, it is preferable to change the communication speed to a low speed. In this manner, power applied to the communication can be effectively used by a slow-down or speed-up of the communication speed.

Figure 14:
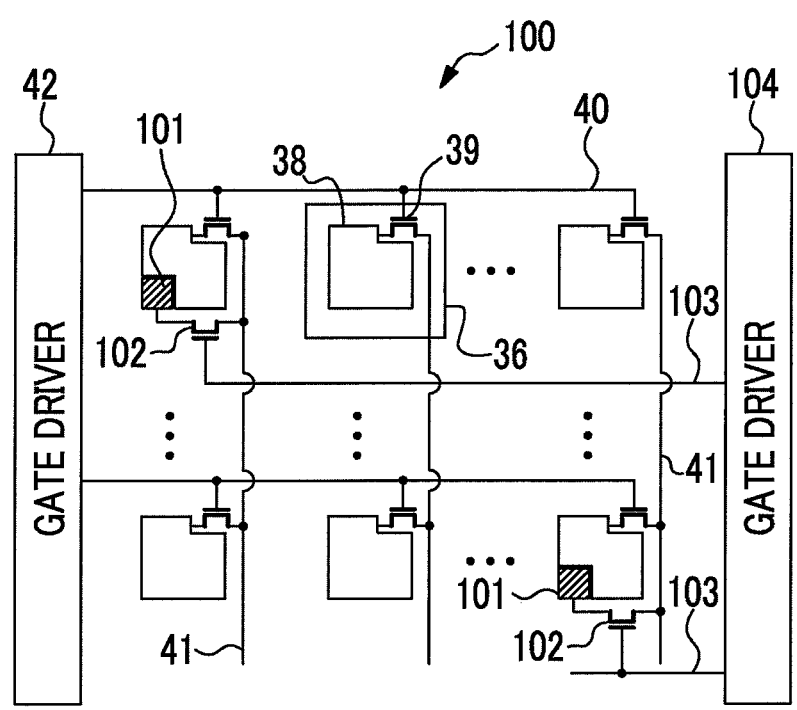
FIG. 14 is a view showing another state of FPD.

In the above embodiment, while the configurations of the pixel 36 and the detection pixel 58 such as size are the same, as in a FPD 100 shown in FIG. 14, a part of the photodiode 38 of the pixel 36 may be a detection pixel 101. As in the above embodiment, a TFT 102, a scanning line 103 and a gate driver 104 are connected to the detection pixel 101 separately from the TFT 39 of the pixel 36, the scanning line 40 and the gate driver 42, and accumulated charge can be read-out from the signal line 41 independent of the pixel 36. A driving method is the same as in the above embodiment. However, at the time of the read-out operation, a column in which the detection pixel 101 is present outside of the lighting field applies the gate pulse to the scanning lines 40 and 103 at the same time, and reads out the pixel 36 and the detection pixel 101 at the same time. Then, an image signal in which the accumulated charge of the pixel 36 is mixed with the accumulated charge of the detection pixel 101 is obtained. The image signal has almost the same value as that of the pixel 36 without the detection pixel 101. Meanwhile, a column in which the detection pixel 101 is present in the lighting field reads out the image signal only from the pixel 36, and makes up for the image signal based on an area ratio and an output ration of the pixel 36 and the detection pixel 101.

A pixel in which the photodiode is directly connected to the signal line without using the TFT maybe provided and used as a detection pixel. In this case, irrespective of the operation of the gate driver, charge accumulated in the detection pixel continuously flows into the signal processing circuit through the signal line.

In addition, using a current flowing to the bias line supplying bias voltage to each pixel based on the charge generated in the pixel, the current of the bias line connected to a certain pixel is monitored and a radiation dose may be detected based on leak charge leaked from the pixel when all TFTs are turned off. Moreover, an AEC detection pixel in which the configuration is different and the output is independent separately from the pixel may be provided on the same plane as the radiographing surface. Furthermore, even when a radiation dose detection sensor such as a well-known ion chamber (ionization chamber) separate from the electronic cassette is used, the present invention is also effective.

In the above embodiment, when the integrated value of the radiation dose detection signal reaches the irradiation stop threshold value, the output of the irradiation continuation signal is stopped. However, when the accumulated radiation dose of the X-ray reaches the target value, expected time is calculated based on the integrated value of the radiation dose detection signal in the comparison circuit 76. When the calculated expected time is up, the output of the irradiation continuation signal may be stopped.

In the above embodiment, an example in which the console 14 and the electronic cassette 13 are separately provided is described. However, the console 14 does not need to be a separate device and the function of the console 14 may be attached to the electronic cassette 13. Similarly, a device in which the radiation source control device 11 and the console 14 are integrated may be used. In addition, there is no limitation to the electronic cassette that is a portable X-ray image detection device, and the present invention is applicable to the X-ray image detection device which is a fixed type to the radiographic stand.

The present invention is not limited the X-rays. The present invention is also applicable to radiographic systems using radiations such as γ-rays.

What is claimed is:

1. A radiographic system comprising:
   a radiation source which irradiates a subject with X-ray radiation;
   a control device which controls a start and stop of X-ray radiation irradiation by the radiation source;
   a radiological image detection device having a detection panel in which pixels accumulating charge according to a reached radiation dose are arranged;
   a radiation dose detection sensor which detects the reached radiation dose; and
   an automatic exposure control unit including a comparison circuit which compares an integrated value of the reached radiation dose detected by the radiation dose detection sensor and a threshold value set beforehand, and determines whether the integrated value of the reached radiation dose reaches a target value based on the comparison result,
   wherein the comparison circuit continuously transmits an irradiation continuation signal which makes the radiation source continue radiation irradiation to the control device until it is determined that the integrated value of the reached radiation dose reaches the target value from the start of the X-ray radiation irradiation by the radiation source, and
   the control device stops the X-ray radiation irradiation when the irradiation continuation signal is not received.

2. The radiographic system according to claim 1,
   wherein the automatic exposure control unit transmits and receives the irradiation continuation signal from and to the control device wirelessly.

3. The radiographic system according to claim 2,
   wherein the automatic exposure control unit and the control device exchange the irradiation continuation signal by ad-hoc communication.

4. The radiographic system according to claim 2,
   wherein the automatic exposure control unit and the control device exchange the irradiation continuation signal by a beacon.

5. The radiographic system according to claim 1,
   wherein the control device is a radiation source control device which is connected with the radiation source and controls driving of the radiation source.

6. The radiographic system according to claim 1,
   wherein the control device is a detection control device which is connected with the radiological image detection device and controls driving of the radiological image detection device, and transmits a signal synchronized with the irradiation continuation signal to a radiation source control device which is connected with the radiation source and controls driving of the radiation source.

7. The radiographic system according to claim 6,
   wherein the detection control device transmits and receives the signal synchronized with the irradiation continuation signal to and from the radiation source control device by wire.

8. The radiographic system according to claim 1,
   wherein the control device is a detection control device which is connected with the radiological image detection device and controls driving of the radiological image detection device, and transmits an irradiation stop signal which stops X-ray radiation irradiation to a radiation source control device which is connected with the radiation source and controls driving of the radiation source by wire when the irradiation continuation signal is not received.

9. The radiographic system according to claim 1,
   wherein the automatic exposure control unit provides an ID of the radiological image detection device in use to the irradiation continuation signal, and
   the control device includes a storage unit that stores an ID of the radiological image detection device in use, which is acquired separately from the irradiation continuation signal, and a collation unit that collates the ID stored in the storage unit with the ID provided to the received irradiation continuation signal and determines whether the received irradiation continuation signal is transmitted to the collation unit itself.

10. The radiographic system according to claim 1, further comprising:
    an irradiation stop determination unit which determines that the X-ray radiation irradiation from the radiation source is stopped based on the reached radiation dose detected by the radiation dose detection sensor.

11. The radiographic system according to claim 10, further comprising:
    a warning display unit which notifies, when the irradiation stop determination unit determines that the X-ray radiation irradiation is stopped before the integrated value of the reached radiation dose reaches a target value, the purport to an operator.

12. The radiographic system according to claim 10,
    wherein when the irradiation stop determination unit determines that the X-ray radiation irradiation is stopped before the integrated value of the reached radiation dose reaches a target value, the control device controls driving of the radiation source so that a subject is additionally irradiated with the X-ray radiation that makes up for a shortage of the reached radiation dose.

13. The radiographic system according to claim 1,
wherein the radiation dose detection sensor and the automatic exposure control unit are built in the radiological image detection device.

14. The radiographic system according to claim 13,
wherein the radiation dose detection sensor is a part of the pixels.

15. The radiographic system according to claim 13,
wherein the radiological image detection device performs a communication function of a signal between the automatic exposure control unit and the control device and a communication function of other signals with one communication I/F.

16. The radiographic system according to claim 15,
wherein the communication I/F is capable of changing a communication speed such that the signal communication between the automatic exposure control unit and the control device is performed at a high speed and other signal communication is performed at a low speed in comparison with the case of the signal between the automatic exposure control unit and the control device.

17. The radiographic system according to claim 13,
wherein the radiological image detection device performs a communication function of a signal between the automatic exposure control unit and the control device and a communication function of other signals with separate communication I/Fs.

18. The radiographic system according to claim 17,
wherein when the communication of the signal between the automatic exposure control unit and the control device is performed, the communication I/F function of other signals is stopped.

19. The radiographic system according to claim 1,
wherein the radiological image detection device is an electronic cassette in which the detection panel is contained in a portable case.

20. A drive control method for a radiographic system including a radiation source which irradiates a subject with X-ray radiation, a control device which controls a start and stop of X-ray radiation irradiation by the radiation source, a radiological image detection device having a detection panel in which pixels accumulating charge according to a reached radiation dose are arranged, a radiation dose detection sensor which detects the reached radiation dose, and an automatic exposure control unit including a comparison circuit which compares an integrated value of the reached radiation dose detected by the radiation dose detection sensor and a threshold value set beforehand, and determines whether the integrated value of the reached radiation dose reaches a target value based on the comparison result, the method comprising:
continuously transmitting, by said comparison circuit, an irradiation continuation signal which makes the radiation source continue X-ray radiation irradiation to the control device from the automatic exposure control unit until it is determined that the integrated value of the reached radiation dose reaches the target value from the start of the X-ray radiation irradiation by the radiation source; and
making the control device stop the X-ray radiation irradiation when the control device does not receive the irradiation continuation signal.

21. A non-transitory computer readable recording medium recorded with a drive control program of a radiographic system including a radiation source which irradiates a subject with X-ray radiation, a control device which controls a start and stop of X-ray radiation irradiation by the radiation source, a radiological image detection device having a detection panel in which pixels accumulating charge according to a reached radiation dose are arranged, a radiation dose detection sensor which detects the reached radiation dose, and an automatic exposure control unit including a comparator which compares an integrated value of the reached radiation dose detected by the radiation dose detection sensor and a threshold value set beforehand, and determines whether the integrated value of the reached radiation dose reaches a target value based on the comparison result, the program causing a computer to execute functions of:
continuously transmitting, by said comparator, an irradiation continuation signal which makes the radiation source continue X-ray radiation irradiation to the control device from the automatic exposure control unit until it is determined that the integrated value of the reached radiation dose reaches the target value from the start of the X-ray radiation irradiation by the radiation source; and
making the control device stop the X-ray radiation irradiation when the control device does not receive the irradiation continuation signal.

22. A radiological image detection device having a detection panel in which pixels accumulating charge according to a reached radiation dose are arranged, the device comprising:
an automatic exposure control unit including a comparison circuit which compares an integrated value of the reached radiation dose detected by a radiation dose detection sensor and a threshold value set beforehand, and determines whether the integrated value of the reached radiation dose reaches a target value based on the comparison result,
wherein the automatic exposure control unit continuously transmits, by said comparison circuit, an irradiation continuation signal which makes a radiation source continue X-ray radiation irradiation to a control device that controls a start and stop of X-ray radiation irradiation by the radiation source until it is determined that the integrated value of the reached radiation dose reaches the target value from the start of the X-ray radiation irradiation by the radiation source.

* * * * *